(12) United States Patent
Teramura

(10) Patent No.: US 7,852,484 B2
(45) Date of Patent: Dec. 14, 2010

(54) LIGHT CONTROL UNIT, OPTICAL TOMOGRAPHIC IMAGING METHOD AND APPARATUS

(75) Inventor: Yuichi Teramura, Kanagawa-ken (JP)

(73) Assignee: Fujifilm Corporation, Tokyo (JP)

( * ) Notice: Subject to any disclaimer, the term of this patent is extended or adjusted under 35 U.S.C. 154(b) by 418 days.

(21) Appl. No.: 11/952,369

(22) Filed: Dec. 7, 2007

(65) Prior Publication Data

US 2008/0140325 A1 Jun. 12, 2008

(30) Foreign Application Priority Data

Dec. 7, 2006 (JP) .............................. 2006-330879

(51) Int. Cl.
*G01B 9/02* (2006.01)
*G01B 11/02* (2006.01)

(52) U.S. Cl. ..................................... 356/479; 356/497
(58) Field of Classification Search ................ 356/479, 356/497; 372/6, 20, 68
See application file for complete search history.

(56) References Cited

U.S. PATENT DOCUMENTS

| | | | | |
|---|---|---|---|---|
| 6,160,826 | A * | 12/2000 | Swanson et al. | 372/20 |
| 6,359,724 | B1 * | 3/2002 | Katagiri et al. | 359/333 |
| 6,665,320 | B1 | 12/2003 | Arbore et al. | |
| 7,019,838 | B2 * | 3/2006 | Izatt et al. | 356/479 |
| 7,148,970 | B2 * | 12/2006 | de Boer | 356/497 |
| 7,391,520 | B2 * | 6/2008 | Zhou et al. | 356/479 |
| 7,508,523 | B2 * | 3/2009 | Chang et al. | 356/479 |
| 7,554,668 | B2 * | 6/2009 | Zhou et al. | 356/479 |
| 2006/0132790 | A1 * | 6/2006 | Gutin | 356/479 |

FOREIGN PATENT DOCUMENTS

| | | |
|---|---|---|
| JP | 2001-264246 A | 9/2001 |
| JP | 2002-214125 A | 7/2002 |
| JP | 2006-047264 A | 2/2006 |

OTHER PUBLICATIONS

Mitsuo Takeda, "Optical Frequencey Scanning Interference Microscopes", Optics Engineering Contact, 2003, pp. 426-432, vol. 41, No. 1

* cited by examiner

*Primary Examiner*—Patrick J Connolly
(74) *Attorney, Agent, or Firm*—Sughrue Mion, PLLC

(57) ABSTRACT

A light control unit that combines and outputs a plurality of light beams, including: a light emission section capable of outputting three or more light beams swept in wavelength within different wavelength ranges from each other; a wavelength combining section having wavelength selectivity, that combines and outputs at least two of the three or more light beams; and a control section that performs control in the light emission section, or upstream or downstream of the wavelength combining section in the optical path of the light beams to cause at least one light beam is outputted during a time period which is different from a time period in which another one or more light beams are outputted, thereby two or more light beams having different wavelengths from each other are combined and outputted at the same time.

6 Claims, 12 Drawing Sheets

LIGHT CONTROL UNIT, OPTICAL TOMOGRAPHIC IMAGING METHOD AND APPARATUS

BACKGROUND OF THE INVENTION

1. Field of the Invention

The present invention relates to an optical tomographic imaging method and apparatus for obtaining a tomographic image of a measuring object by OCT (optical coherence tomography) measurement, and a light control unit applicable to the optical tomographic imaging apparatus.

2. Description of the Related Art

An optical tomographic image obtaining system using OCT measurement is sometimes used to obtain an optical tomographic image of a living tissue. In the optical tomographic image obtaining system, a low coherence light beam outputted from the light source is split into measuring and reference beams, and the measuring beam is irradiated onto a measuring object, then the reflected beam from the measuring object or backscattered light when the measuring beam is irradiated thereon is combined with the reference beam, and an optical tomographic image is obtained based on the intensity of the interference beam between the reflected beam and the reference beam. Hereinafter, reflected beam from a measuring object and backscattered light are collectively referred to as the "reflected beam".

The OCT measurement is largely categorized into TD-OCT (Time Domain OCT) measurement and FD (Fourier Domain)-OCT measurement. The TD-OCT measurement is a method for obtaining a reflected beam intensity distribution corresponding to a position in the depth direction (depth position) of a measuring object by measuring interference beam intensity while changing the optical path length of the reference light.

The FD-OCT measurement is a method for obtaining a reflected light intensity distribution corresponding to a depth position of a measuring object by measuring interference beam intensity with respect to each spectral component of the beam without changing the optical path length of the reference beam, and performing frequency analysis, typically a Fourier transform, on the obtained spectral interference intensity signals using a computer. The FD-OCT does not require the mechanical scanning used in TD-OCT, so that it has been drawing wide attention as a method that allows high speed measurement.

Typical systems that use FD-OCT measurement are SD-OCT (Spectral Domain OCT) system and SS-OCT (Swept Source OCT) system. The SD-OCT system uses a broadband and low coherence light beam, such as SLD (Super Luminescence Diode), ASE (Amplified Spontaneous Emission), or white light beam, as the light source, and forms an optical tomographic image in the following manner. The broadband and low coherence light beam is split into measuring and reference beams using Michelson interferometer or the like and the measuring beam is irradiated onto a measuring object, then a reflected beam from the measuring object when the measuring beam is irradiated thereon is caused to interfere with the reference beam and the interference beam is broken down into frequency components using a spectroscopic device, thereafter the intensity of the interference beam with respect to each frequency component is measured using a detector array including elements, such as photodiodes, disposed in an array and an optical tomographic image is formed by performing Fourier transform on the obtained spectral interference signals using a computer.

In the mean time, the SS-OCT system uses a laser that temporally sweeps the optical frequency, in which the reflected beam is caused to interfere with the reference beam at each wavelength, then the temporal waveform of the signal corresponding to the temporal change in the optical frequency is measured and an optical tomographic image is formed by performing Fourier transform on the obtained spectral interference signals using a computer.

In various types of OCT measurements described above, a broader wavelength range of the light source and increased number of corresponding data points are desired in order to improve spatial resolution and to obtain a high quality image. The conventional Fourier transform method requires a light source having a continuous spectrum. As for the light source, a semiconductor light source, such as a small and inexpensive superluminescence diode (SLD), semiconductor optical amplifier, or the like, is desirable. But, the gain bandwidths of these devices are limited due to their medium characteristics, so that it is difficult to realize a continuous bandwidth exceeding 100 nm with a single device.

Consequently, a method for broadening the wavelength range by combining light beams outputted from a plurality of light sources are disclosed, as described, for example, in Japanese Unexamined Patent Publication No. 2002-214125. As a broadband spectrum light source, the method uses a plurality of light sources that output light beams having different spectral ranges with each other, and light beams outputted from respective light sources are combined using an optical coupler to output a single wave beam.

For the SD-OCT measurement, a method for forming a continuous spectrum by combining light beams from a plurality of gain media, each having a overlapping wavelength range with each other, is disclosed in Japanese Unexamined Patent Publication No. 2001-264246. As for the method of forming a continuous spectrum through wavelength combination for SS-OCT, a structure including a plurality of wavelength scanning light sources, each having a gain medium and a wavelength selection element is disclosed in Japanese Unexamined Patent Publication No. 2006-047264. Further, U.S. Pat. No. 6,665,320 discloses a structure that simultaneously controls light beams from a plurality of gain media using a single wavelength selection element.

With regard to increasing the data points, the interference beams are generally detected with respect to each wavelength using a detector array including elements, such as photodiodes, disposed in an array, so that the number of data points is limited by the number of elements of the detector array in the SD-OCT system. At present, it is not desirable to increase the number of elements of the detector array for increasing the number of data points, since such increase would result in cost increase, decreased manufacturability, reduced measuring rate, and the like. On the other hand, in the SS-OCT system, in order to increase the number of data points, for example, it is just necessary to increase the sampling frequency of the circuit that converts an optical current signal from the detector to a digital value if the frequency sweep period of the light source is assumed to be constant, so that it may be realized easily at low cost with a high measuring rate.

When combining a plurality of light sources in order to obtain high spatial resolution as described above, if the light beams outputted from the plurality of light sources are combined using, for example, a coupler with a branching ratio of 50:50, the light utilization efficiency is degraded since the total output is reduced to a half by the coupler. Another method is to combine the light beams using a polarization beam splitter, but this method allows beam combination of up to only two beams, thereby bandwidth broadening is limited.

Further, where light beams from a plurality of light sources are combined and used, the conventional SS-OCT system poses a problem that, when light beams having different wavelengths are outputted from a plurality of light sources and irradiated onto a measuring object at the same time, the interference information provided by the plurality of light beams is mixed up and unable to be detected since the detector of the system includes only a single element.

For this reason, in the systems described in Japanese Unexamined Patent Publication No. 2006-047264, and U.S. Pat. No. 6,665,320, a configuration is adopted in which only a single wavelength is inputted to the detector at a time by controlling the light source or using a switching element. Such method, however, poses a problem that the measuring rate is reduced since it takes time to irradiate all of the wavelengths of the measuring beam, though it may provide a broadband beam as the measuring beam.

Therefore, in the OCT measurement, if it is possible to use a plurality of light beams having different wavelengths at the same time and to obtain interference information with respect to each of the light beams at the same time by separating the interference information provided by the plurality of light beams, a high resolution measurement may be performed with a high measurement rate. As such, an optical tomographic imaging method and apparatus having such capabilities have been demanded.

The present invention has been developed in view of the circumstances described above, and it is an object of the present invention to provide an optical tomographic imaging method and apparatus capable of obtaining a high resolution tomographic image rapidly.

SUMMARY OF THE INVENTION

A light control unit of the present invention is a unit that combines and outputs a plurality of light beams, the unit including:

a light emission section capable of outputting three or more light beams swept in wavelength within different wavelength ranges from each other;

a wavelength combining means having wavelength selectivity, that combines and outputs at least two of the three or more light beams; and a control means that performs control in the light emission section, or upstream or downstream of the wavelength combining means in the optical path of the light beams to cause at least one light beam is outputted during a time period which is different from a time period in which another one or more light beams are outputted, wherein two or more light beams having different wavelengths from each other are combined and outputted at the same time.

Preferably, the wavelength ranges of at least two of the three or more light beams are separated from each other, the wavelength ranges of at least two of the three or more light beams are partially overlapping with each other, and the control means is a means that causes the light beams having separate wavelength ranges to be outputted during the same time period, and the light beams having partially overlapping wavelength ranges to be outputted during different time periods.

A first optical tomographic imaging apparatus of the present invention is an apparatus, including:

a beam splitting means that splits each of the light beams outputted from the light control unit into a measuring beam and a reference beam;

a beam combining means that combines the reference beams with reflected beams from a measuring object when the measuring beams are irradiated on the measuring object with respect to each of the light beams;

an interference beam detection means that detects interference beams produced when the reflected beams are combined with the reference beams by the beam combining means as interference signals with respect to each of the light beams; and a tomographic image processing means that generates a tomographic image of the measuring object using the interference signals.

A second optical tomographic imaging apparatus of the present invention is an apparatus, including:

a light emission section capable of outputting three or more light beams swept in wavelength within different wavelength ranges from each other, and outputs at least two or more of the three or more light beams;

a beam splitting means that splits each of the light beams outputted from the light emission section into a measuring beam and a reference beam;

a wavelength combining means having wavelength selectivity, that combines and outputs at least two of a plurality of split measuring beams;

a control means that performs control in the light emission section, or upstream or downstream of the wavelength combining means in the optical path of the measuring beams to cause at least one measuring beam is irradiated on a measuring object during a time period which is different from a time period in which another one or more measuring beams are irradiated, and two or more measuring beams having different wavelengths from each other to be combined and irradiated on the measuring object at the same time;

a beam combining means that combines the reference beams with reflected beams from the measuring object when the combined measuring beams are irradiated on the measuring object with respect to each of the light beams;

an interference beam detection means that detects interference beams produced when the reflected beams are combined with the reference beams by the beam combining means as interference signals with respect to each of the light beams; and a tomographic image processing means that generates a tomographic image of the measuring object using the interference signals.

An optical tomographic imaging method of the present invention is a method, including the steps of:

providing a light emission section capable of outputting three or more light beams swept in wavelength within different wavelength ranges from each other, and outputs at least two or more of the three or more light beams;

splitting each of the light beams outputted from the light emission section into a measuring beam and a reference beam;

combining and outputting at least two of a plurality of split measuring beams using a wavelength combining means having wavelength selectivity;

causing, in the light emission section, or upstream or downstream of the wavelength combining means in the optical path of the measuring beams, at least one measuring beam to be irradiated on a measuring object during a time period which is different from a time period in which another one or more measuring beams are irradiated, and two or more measuring beams having different wavelengths from each other to be combined and irradiated on the measuring object at the same time;

combining the reference beams with reflected beams from the measuring object when the combined measuring beams are irradiated on the measuring object with respect to each of the light beams;

detecting interference beams produced when the reflected beams are combined with the reference beams as interference signals with respect to each of the light beams; and generating a tomographic image of the measuring object using the interference signals.

Preferably, in the second optical tomographic imaging apparatus and the optical tomographic imaging method described above, the wavelength ranges of at least two of the three or more light beams are separated from each other, the wavelength ranges of at least two of the three or more light beams are partially overlapping with each other, and the measuring beams having separate wavelength ranges are irradiated on the measuring object during the same time period and the measuring beams having partially overlapping wavelength ranges are irradiated on the measuring object during different time periods.

The referent of "different wavelength ranges" as used herein means to include not only those separated from each other but also those partially overlapping with each other unless the entire wavelength ranges are identical. The widths of the wavelength ranges of the respective light beams may be the same or different.

The wavelength range of each light beam may be such that a continuous spectrum is formed by the three or more light beams which the light emission section is capable of outputting, or may be such that a discontinuous spectrum is formed thereby. Further, the light emission section may include three or more light sources, each outputting a single light beam, or may include a single or a plurality of light sources, each outputting a plurality of light beams.

The referent of "wavelength combining means having wavelength selectivity" as used herein means a wavelength combining means having optical transmittance or reflectance that changes according to wavelength and, in general, it means those structured so as to be able to efficiently combine light beams within a predetermined wavelength range. As for the wavelength combining means having wavelength selectivity, a WDM (Wavelength Division Multiplexing) coupler, a dichroic mirror, a dichroic prism, a diffractive optical element, or the like may be used.

As for the control means, for example, a control means that performs current ON/OFF control of the light emission section if the section is formed of a device that emits light by current injection, a shutter that blocks the optical path, an optical switch means that changes the optical path, or the like may be used.

The referent of "wavelength ranges of two light beams are separated from each other" as used herein means that a low intensity wavelength region that does not contribute to the OCT measurement appears between the peak wavelengths of two light beams where the light intensity falls below or to about −10 dB with respect to the peak intensity of the two light beams. If the two light beams have different peak intensities, the lower peak intensity is used for this purpose. The referent of "wavelength ranges of two light beams are partially overlapping with each other" has the opposite meaning to the referent of "wavelength ranges of two light beams are separated from each other" described above.

Likewise, the referent of "discontinuous spectrum" as used herein means that a wavelength region extending substantially wide in comparison with a sampling interval of frequency range measured in the FD-OCT measurement appears within the wavelength range of a particular light beam where the light intensity falls below or to about −10 dB with respect to the peak intensity of the particular light beam. The referent of "continuous spectrum" has the opposite meaning to the referent of "discontinuous spectrum" described above. It is noted that, for example, in a light beam formed by modulating the frequency of a semiconductor laser in a staircase pattern, or in a broadband light of densely arranged line spectra formed by, for example, frequency comb technology, the wavelength spacing is smaller than or equal to the sampling interval of frequency range measured in the FD-OCT measurement, so that such spectra may be regarded as continuous spectra.

Further, the referent of "spectrum" of swept light beam as used herein does not mean an instantaneous light intensity, but a light intensity distribution in the total sweep time unless otherwise specifically described.

According to the light control unit of the present invention, a broadband spectrum may be obtained by efficiently combining a plurality of light beams outputted from the light emission section with the wavelength combining means having wavelength selectivity. Further, the light control unit of the present invention includes a control means that performs control to cause at least one light beam is outputted during a time period which is different from a time period in which another one or more light beams are outputted, and thereby two or more light beams having different wavelengths from each other are combined and outputted at the same time. This allows a plurality of light beams that may cause mixing of interference signals to be outputted during different time periods, and two or more light beams having different wavelengths to be outputted at the same time, so that the light control unit of the present invention may be suitably used for the SS-OCT measurement.

According to the first optical tomographic imaging apparatus of the present invention, the apparatus employs the light control unit described above, so that it may use efficiently combined broadband light as the measuring light, and high resolution measurement may be performed. Further, according to the first optical tomographic imaging apparatus of the present invention, two or more light beams having different wavelengths are outputted from the light control unit, then each of the light beams outputted from the light control unit is split into a measuring beam and a reference beam, the reference beams are combined with reflected beams from a measuring object when the measuring beams are irradiated on the measuring object with respect to each of the light beams, and interference beams produced when the reflected beams are combined with the reference beams are detected as interference signals with respect to each of the light beams. This may prevent a plurality of interference signals, produced by a plurality of interference beams when a plurality of light beams having different wavelengths is irradiated on the measuring object at the same time, from being mixed up, and a plurality of interference signals is obtained at the same time with respect to each of the light beams. Thus, the measuring rate may be increased in comparison with the past, and a high resolution tomographic image may be obtained rapidly.

In this respect, if the wavelength ranges of at least two of the three or more light beams are separated from each other, the wavelength ranges of at least two of the three or more light beams are partially overlapping with each other, and the control means is a means that causes the light beams having separate wavelength ranges to be outputted during the same time period, and the light beams having partially overlapping wavelength ranges to be outputted during different time periods, then the reference beams and reflected beams having separate wavelength ranges produced during the same time period may be separated from each other using the separation means having wavelength selectivity, and the reference beams and reflected beams having partially overlapping wavelength ranges may be separated from each other according to the time. Thus, the interference beams may be reliably separated from each other and detected with respect to each of the light beams.

According to the second optical tomographic imaging apparatus of the present invention or the optical tomographic imaging method of the present invention, a light emission section which is capable of outputting three or more light beams and outputs at least two or more of the three or more light beams is used, then each of the light beams outputted from the light emission section is split into a measuring beam and a reference beam, and at least two of a plurality of split measuring beams are combined using a wavelength combining means having wavelength selectivity, so that efficiently combined broadband light may be used as the measuring light, allowing high resolution measurement. Further, according to the second optical tomographic imaging apparatus of the present invention or the optical tomographic imaging method of the present invention, two or more measuring beams having different wavelengths from each other are irradiated on a measuring object at the same time, and the reference beams are combined with reflected beams from the measuring object when the combined measuring beams are irradiated on the measuring object with respect to each of the light beams, and interference beams produced when the reflected beams are combined with the reference beams are detected as interference signals with respect to each of the light beams. This may prevent a plurality of interference signals, produced by a plurality of interference beams when a plurality of light beams having different wavelengths is irradiated on the measuring object at the same time, from being mixed up, and a plurality of interference signals is obtained at the same time with respect to each of the light beams. Thus, the measuring rate may be increased in comparison with the past, and a high resolution tomographic image may be obtained rapidly.

In this respect, if the wavelength ranges of at least two of the three or more light beams are separated from each other, the wavelength ranges of at least two of the three or more light beams are partially overlapping with each other, and the measuring beams having separate wavelength ranges are irradiated on the measuring object during the same time period, then the reference beams and reflected beams having separate wavelength ranges produced during the same time period may be separated from each other using the separation means having wavelength selectivity, and the reference beams and reflected beams having partially overlapping wavelength ranges may be separated from each other according to the time. Thus, the interference beams may be reliably separated from each other and detected with respect to each of the light beams.

DESCRIPTION OF THE PREFERRED EMBODIMENTS

Figure 1:
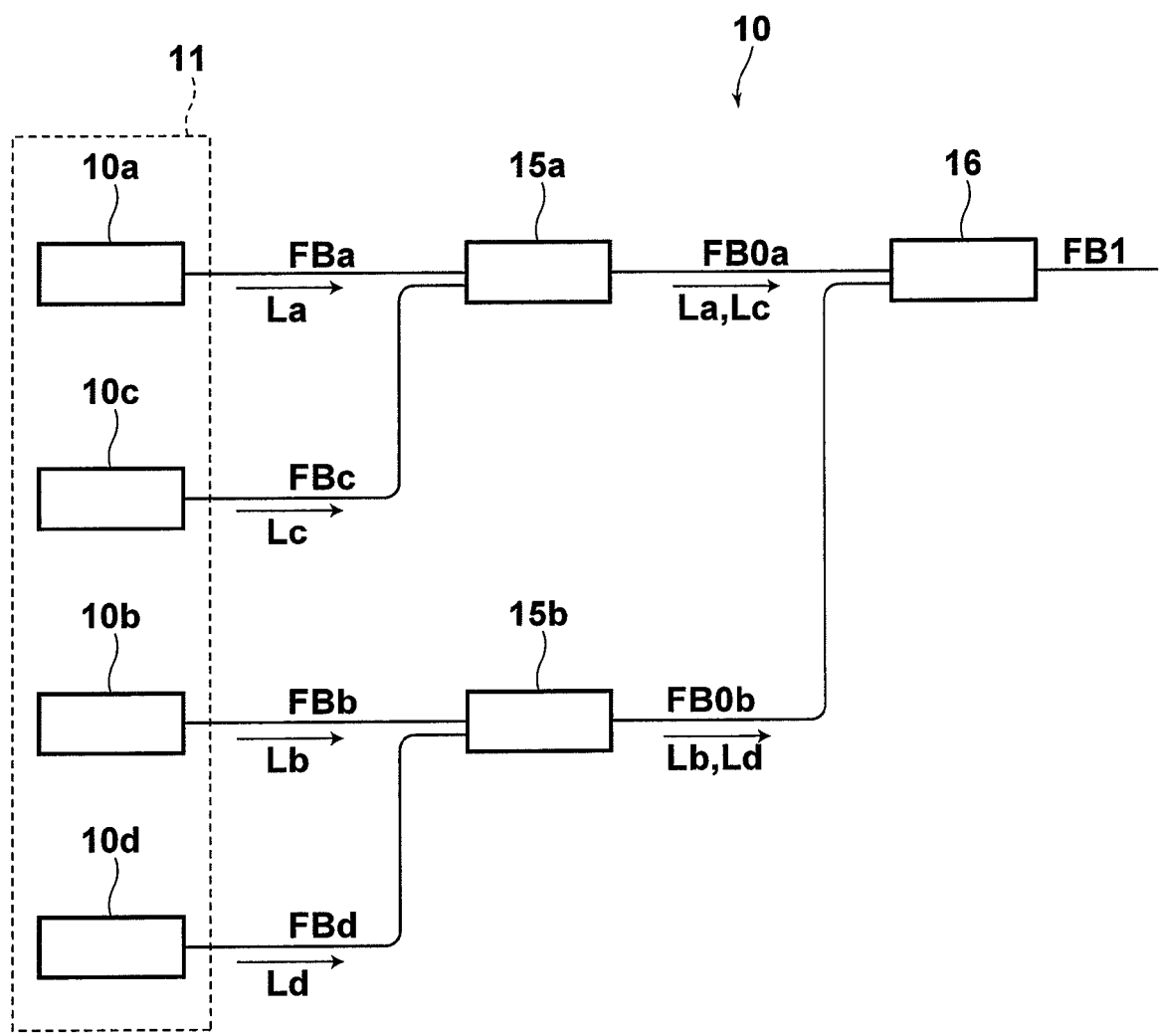
FIG. 1 is a schematic configuration diagram of the light source unit according to a first embodiment of the present invention.
Figure 2:
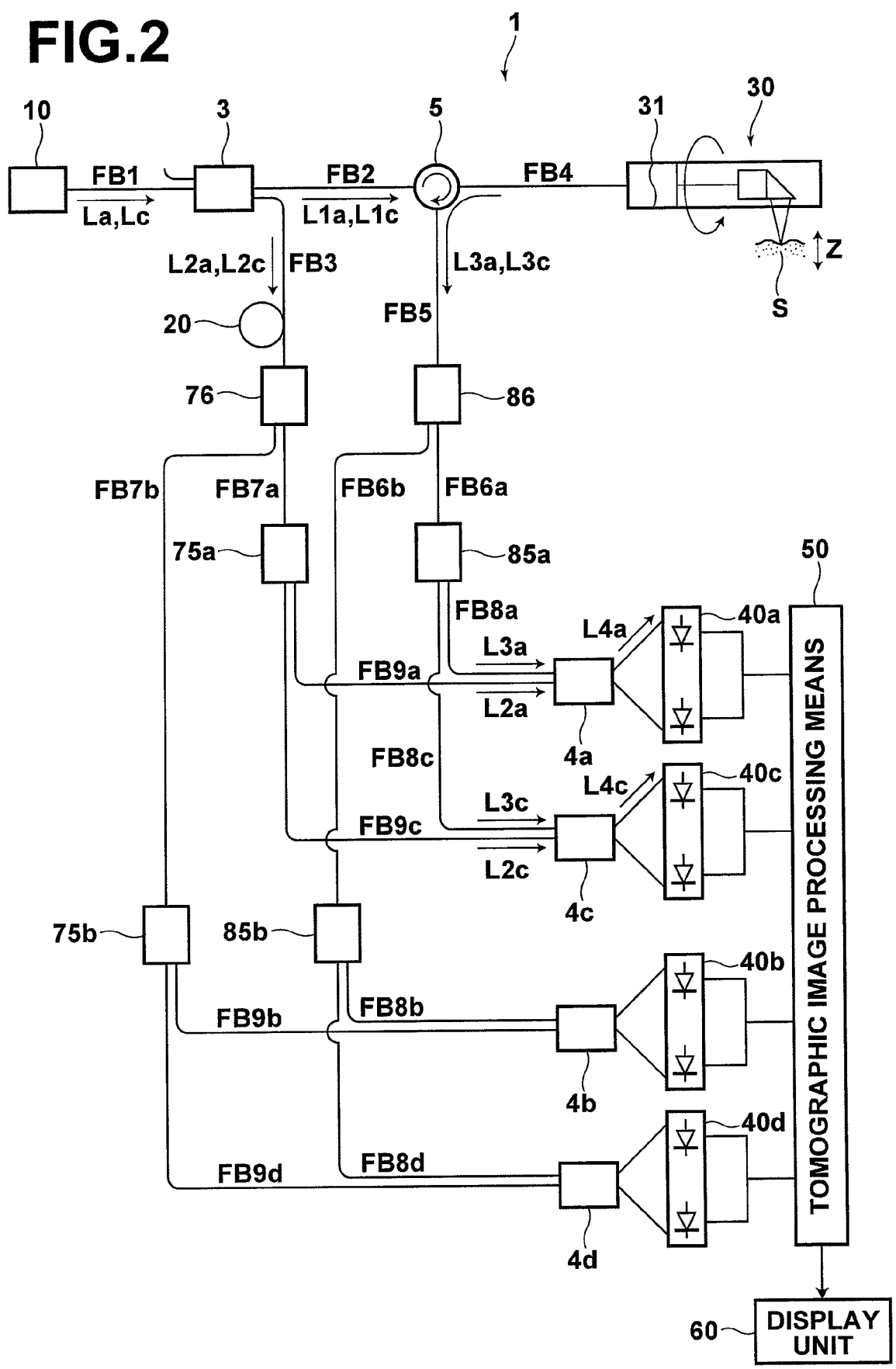
FIG. 2 is a schematic configuration diagram of the optical tomographic imaging apparatus according to a first embodiment of the present invention.

Hereinafter, embodiments of the light control unit, optical tomographic imaging method and apparatus will be described in detail. FIG. 1 is a schematic configuration diagram of the light source unit 10 according to a first embodiment of the present invention, and FIG. 2 is a schematic configuration diagram of the optical tomographic imaging apparatus 1 including the light source unit 10. The optical tomographic imaging apparatus 1 is, for example, an apparatus that uses a light beam outputted from the light source unit 10 to obtain a tomographic image of a measuring object such as a living tissue or a cell in a body cavity by the aforementioned SS-OCT measurement using a Mach-Zehnder interferometer.

The light source unit 10 will be described first. The light source unit 10 is a unit that combines and outputs a plurality of light beams, having the function of the light control means of the present invention. As illustrated in FIG. 1, the light source unit 10 includes: a light emission section 11 capable of outputting three or more light beams which are swept in wavelength within different wavelength ranges from each other; beam combining means 15a, 15b, which are wavelength combining means, that have wavelength selectivity, and combine and output at least two of the three or more light beams; and a control means 16 which is located downstream of the beam combining means 15a, 15b in the optical path of the light beams and controls the light beams such that at least one light beam is outputted during a time period which is different from a time period in which another one or more light beams are outputted, thereby causing two or more light beams having different wavelengths from each other to be combined and outputted at the same time.

More specifically, in the present embodiment, the light emission section 11 includes four light sources 10a, 10b, 10c, and 10d, which are wavelength swept light sources that output laser beams while sweeping the frequencies (wavelengths) within different wavelength ranges with each other at a constant period. Each of the light sources 10a, 10b, 10c, and 10d may be formed of, for example, an external resonance type wavelength swept light source that includes, as the major components, a gain medium of a semiconductor optical amplifier (SOA), a wavelength selection means of a fiber Fabry-Perot tunable filter (FFP-TF), and an optical fiber connected to both ends of the semiconductor optical amplifier and wavelength selection means for forming a ring-shaped resonator.

Here, the semiconductor optical amplifier has functions, through injection of drive current therein, to output a weak emission light beam to an optical fiber connected to one end thereof and to amplify a light beam inputted from the optical fiber connected to the other end thereof. By the semiconductor optical amplifier, the laser beam is oscillated in the ring-shaped resonator. The oscillated laser beam may be taken out to outside by connecting a branching optical coupler to a part of the optical fiber. Then, by selecting the wavelength of the laser beam oscillating in the resonator by the wavelength selection means, a laser beam swept in wavelength at a constant period may be outputted from each of the light sources 10a, 10b, 10c, and 10d.

Figure 3A:
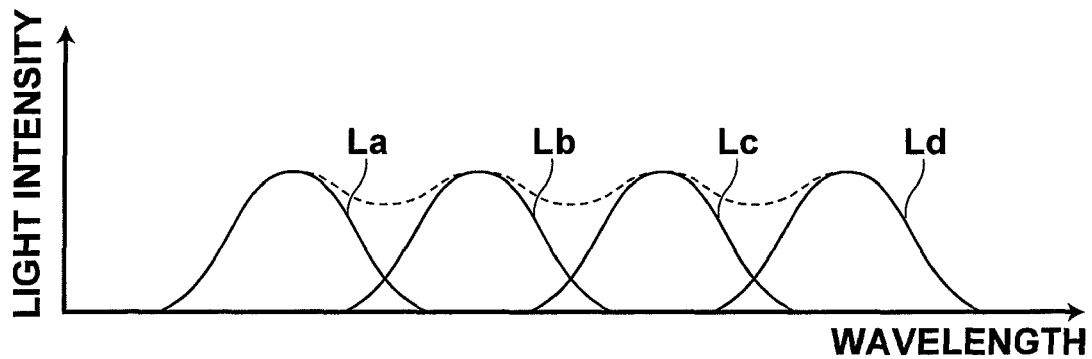
FIGS. 3A to 3C illustrate respective spectra of light beams outputted from the light source unit shown in FIG. 1.

Example spectra of light beams La, Lb, Lc, and Ld outputted from the light sources 10a, 10b, 10c, and 10d respectively are shown in FIG. 3A. The light beams La, Lb, Lc, and Ld have different wavelength ranges with each other. Each light beam has a continuous spectrum within each wavelength range, and the center wavelength of each wavelength range becomes longer in the order of the light beams La, Lb, Lc, and Ld. Of the light beams La, Lb, Lc, and Ld, two light beams adjacent to each other in the order of the center wavelength have partially overlapping wavelength ranges, and the light beams La, Lb, Lc, and Ld together form a continuous spectrum (indicated by a dotted line in FIG. 3A).

Figure 3B:
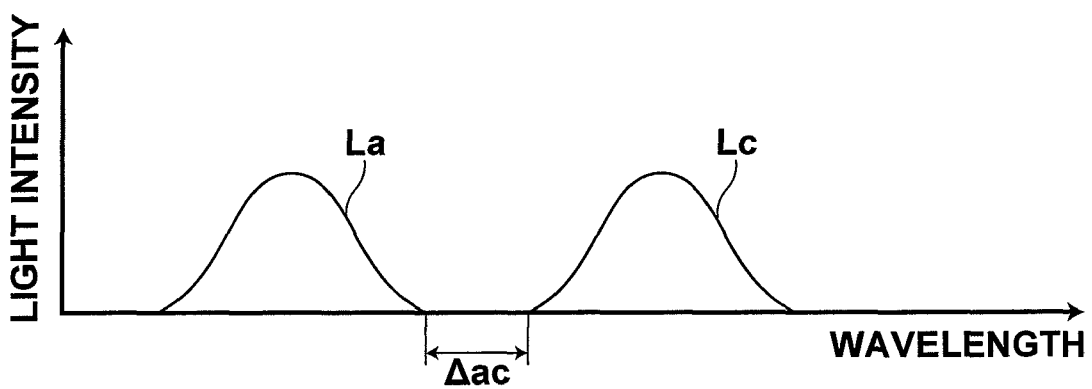
Figure 3C:
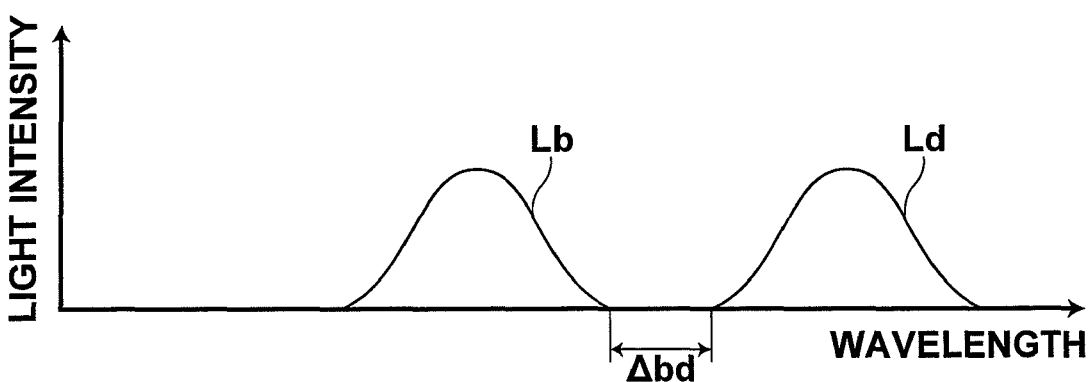

In addition, of the light beams La, Lb, Lc, and Ld, two light beams not adjacent to each other in the order of center wavelength have separate wavelength ranges. That is, the wavelength ranges of the light beams La and Lc are separated by $\Delta ac$ as illustrated in FIG. 3B, and the wavelength ranges of the light beams Lb and Ld are separated by $\Delta bd$ as illustrated in FIG. 3C.

The light sources 10a, 10b, 10c, and 10d are structured such that a wavelength sweep period Ta of the light beam La is equal to that of the light beam Lc, and a wavelength sweep period Tb of the light beam Lb is equal to that of the light beam Ld, but the wavelength sweep period Ta may differ from the wavelength sweep period Tb.

As illustrated in FIG. 1, the output terminals of the light sources 10a, 10c are linked to the input terminal of the beam combining means 15a through optical fibers FBa, FBc respectively, and the output terminals of the light sources 10b, 10d are linked to the input terminal of the beam combining means 15b through optical fibers FBb, FBd respectively.

Each of the beam combining means 15a, 15b has a function to combine light beams according to a predetermined cutoff wavelength, and is formed of, for example, a WDM coupler. The beam combining means 15a combines the light beam La outputted from the light source 10a and the light beam Lc outputted from the light source 10c. The beam combining means 15b combines the light beam Lb outputted from the light source 10b and the light beam Ld outputted from the light source 10d. The cutoff wavelengths of the beam combining means 15a, 15b are set at wavelengths within the $\Delta ac$ and $\Delta bd$ respectively. This allows each light beam to be combined efficiently.

In the present embodiment, the control means 16 has two input terminals and one output terminal, but it may have more input or output terminals. The output terminals of the beam combining means 15a, 15b are linked to the two input terminals of the control means are through optical fibers FB0a, FB0b respectively. An optical fiber FB1 is connected to the output of the control means 16.

The control means 16 is formed of, for example, a switching element, and has a function to output only the light beam inputted from either one of the two input terminals and to block the light beam inputted from the other input terminal, thereby switching the light beams according to the time. More specifically, the control means 16 causes light beams having separate wavelength ranges with each other to be outputted from the light source unit 10 during the same time period, and light beams having partially overlapping wavelength ranges to be outputted from the light source unit 10 during different time periods.

An example operation of the light source unit 10 structured in the manner as described above will now be described. The light beams La, Lc outputted from the light sources 10a, 10c are guided by the optical fibers FBa, FBc respectively, and combined in the beam combining means 15a. The combined two light beams are guided by the optical fiber FB0a and inputted to the control means 16.

The light beams Lb, Ld outputted from the light sources 10b, 10d are guided by the optical fibers FBb, FBd respectively, and combined in the beam combining means 15b. The combined two light beams are guided by the optical fiber FB0b and inputted to the control means 16.

Figure 4:
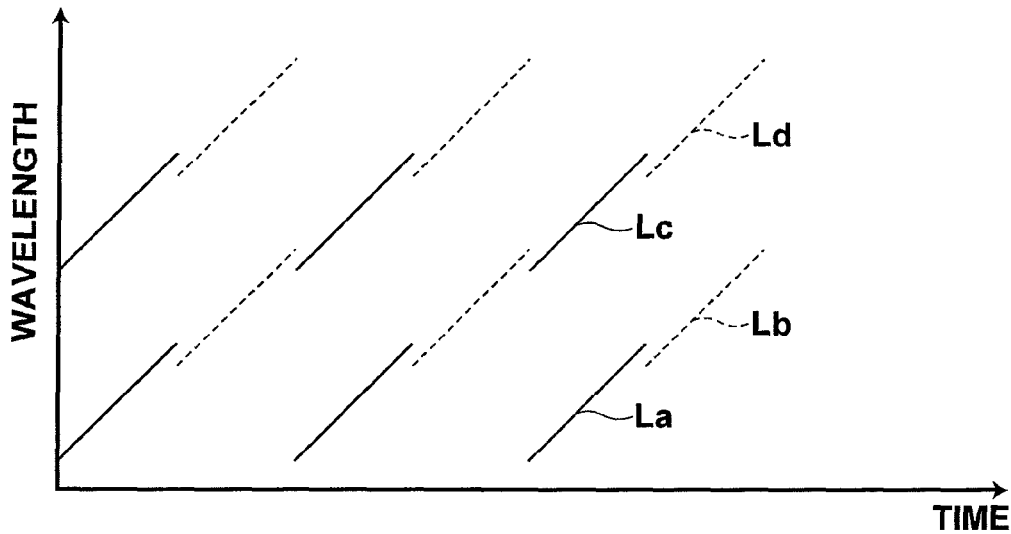
FIG. 4 illustrates wavelength sweep of the light source unit shown in FIG. 1.

All of the light sources are synchronized by a not shown external trigger, and driven to perform wavelength sweep at a constant period. Further, the control means 16 is also synchronized with the sweep period of each light source by the external trigger. FIG. 4 illustrates each of the light beams outputted from the light source unit 10 through control of the control means 16, and the wavelength sweep thereof. In FIG. 4, reference symbols are partly omitted in order to avoid complication, but FIG. 4 illustrates wavelength sweeps of the light beams La (solid lines), Lb (dotted lines), Lc (solid lines), and Ld (dotted lines) in the order from the range of the shortest wavelengths toward the range of longest wavelengths.

As illustrated in FIG. 4, during a single sweep period of the light sources 10a, 10c, the light source unit 10 outputs only the light beams La, Lc, and does not output the light beams Lb, Ld. Thereafter, switching is performed in the control means 16, and during a single sweep period of the light sources 10b, 10d, the light source unit 10 outputs only the light beams Lb, Ld, and does not output the light beams La, Lc. The same is repeated hereinafter.

The optical tomographic imaging apparatus shown in FIG. 2 includes: the light source unit 10 described above; a beam splitting means 3 that splits each of a plurality of light beams having different wavelengths with each other outputted from the light source unit 10 into measuring and reference beams; beam combining means 4a, 4b, 4c, and 4d that combine reflected beams from a measuring object S when the measuring beams are irradiated on the measuring object S with the reference beams with respect to each light beam; interference beam detection means 40a, 40b, 40c, and 40d that detect interference beams produced when the measuring beams are combined with the reference beams as interference signals with respect to each light beam; and a tomographic image processing means 50 that obtains a tomographic image of the measuring object S using the interference signals.

The referent of "with respect to each light beam" as used herein means with respect to each light based on each light beam outputted from the light emission section 11, i.e., with respect each light having the same spectrum.

The beam splitting means 3 is formed of, for example, a 2×2 optical coupler with a branching ratio of 90:10. The beam splitting means 3 splits each of a plurality of light beams having different wavelengths with each other outputted from the light source unit 10 into measuring and reference beams at a ratio of 90:10.

A probe 30 is provided in the optical path of the measuring beams. The probe 30 guides the measuring beams inputted through an optical rotary connector 31 to the measuring object S, and irradiates the measuring beams on the same region at the same time. Further, the probe 30 guides reflected beams from the measuring object S when the measuring beams are irradiated on the measuring object S. The probe 30 is structured such that the fiber section at the distal side of the optical rotary connector 31 is rotated by a not shown motor to circularly scan the beams on the sample, which enables a two dimensional tomographic image measurement. Further, a three dimensional tomographic image measurement is feasible by scanning the tip of the fiber 30 by a not shown motor in the direction orthogonal to the plane formed by the scan circle of the light path. The probe 30 is detachably attached to the optical fiber FB4 through a not shown optical connector. It should be appreciated that the shape of the probe tip and the scanning direction are not limited to those described above. For example, the two dimensional scanning may be performed by providing a high speed scanning mirror at the distal end of the fiber.

An optical path length control means 20 is provided in the optical path of the reference beams. The optical path length control means 20 controls the optical path length of the reference beams to control the starting position for obtaining a tomographic image.

Reference beam separation means 76, 75a, and 75b that separate the reference beams into respective beams are provided in the optical path of the reference beams after the optical path length control means. Reflected beam separation means 86, 85a, and 85b that separate the reflected beams into respective beams are provided in the optical path of the reflected beams.

In the present embodiment, each of the reference beam separation means 76 and reflected beam separation means 86 has a single input terminal and two output terminals, but it may have more input or output terminals. The output terminals of the reference beam separation means 76 and the input terminals of the reference beam separation means 75a, 75b are linked by optical fibers FB7a, FB7b respectively. The output terminals of the reflected beam separation means 86 and the input terminals of the reflected beam separation means 85a, 85b are linked by optical fibers FB6a, FB6b respectively.

Each of the reference beam separation means 76 and reflected beam separation means 86 is formed of, for example, a switching element, and has a function to output the light beams inputted from the input terminal to either one of the two output terminals, thereby switching the output terminals for outputting the light beams according to time. The switching of each of the reference beam separation means 76 and reference beam separation means 86 is performed in synchronization with the sweep period of each light source through the external trigger as in the control means 16.

Each of the reference beam separation means 75a, 75b, and reflected beam separation means 85a, 85b has a function to separate light beams according to a predetermined cutoff wavelength, and is formed of, for example, a WDM coupler. The cutoff wavelengths of the reference beam separation means 75a and reflected beam separation means 85a are set to a wavelength within the wavelength range Δac described above, and the cutoff wavelength of the reference beam separation means 75b and reflected beam separation means 85b are set to a wavelength within the wavelength range Δac described above. The use of the reference beam separation means 75a, 75b, and reflected beam separation means 85a, 85b having such wavelength selectivity as described above allows efficient separation of the respective light beams with respect to each wavelength.

Each of the beam combining means 4a, 4b, 4c, and 4d is formed of, for example, a 2×2 optical coupler with a branching ratio of 50:50. The beam combining means 4a combines the reflected beam L3a and reference beam L2a, which are based on the light beam La, and outputs an interference beam L4a produced at that time to the interference beam detection means 40a. It is noted here that the beam combining means 4a divides the interference beam into halves and outputs to the interference beam detection means 40a, and the interference beam detection means 40a performs balanced detection to detect the halved interference beams. This structure reduces effects of fluctuations in the light intensity so that a clearer image may be obtained.

The beam combining means 4b combines the reflected beam L3b and reference beam L2b, which are based on the light beam Lb, and outputs an interference beam L4b produced at that time to the interference beam detection means 40b. The beam combining means 4c combines the reflected beam L3c and reference beam L2c, which are based on the light beam Lc, and outputs an interference beam L4c produced at that time to the interference beam detection means 40c. The beam combining means 4d combines the reflected beam L3d and reference beam L2d, which are based on the light beam Ld, and outputs an interference beam L4d produced at that time to the interference beam detection means 40d. The beam combining means 4b, 4c, and 4d, and interference beam detection means 40b, 40c, and 40d also structured to perform balanced detection as in the beam combining means 4a and interference beam detection means 40a.

The interference beam detection means 40a, 40b, 40c, and 40d have functions to perform photoelectrical conversions on the inputted interference beams respectively, and to detect the interference beams as a plurality of interference signals ISa, ISb, ISc, and ISd with respect to the wavelength ranges of the respective light beams. At this time, the interference signals ISa, ISb, ISc, and ISd, which are the spectra of the respective light sources 10a, 10b, 10c, and 10d added with the results of Fourier transforms performed on the tomographic information (reflectivity) function, are observed in the interference beam detection means 40a, 40b, 40c, and 40d respectively.

The tomographic image processing means 50 includes a computer system, such as a personal computer. The tomographic image processing means 50 associates the interference signals ISa, ISb ISc, and ISd photoelectrically converted by the interference beam detection means 40 with the oscillation frequencies of the wavelength swept light sources, and performs signal integration so as to become equally frequency spaced interference signals, thereby generating a single broadband interference signal ISO. Then, the tomographic information of the measuring object S at each depth position is obtained by performing a frequency analysis on the interference signal ISO.

Here, a method for generating a tomographic image in the tomographic image processing means 50 based on the interference signal ISO will be described briefly. For more detailed description, reference is made to the literature by M. Takeda, "Optical Frequency Scanning Interference Microscopes", Optics Engineering Contact, Vol. 41, No. 7 pp. 426-432, 2003.

Assuming the light intensity of the interference pattern with respect to each optical path length difference l to be S(l) when the measuring beam is irradiated onto the measuring object S, and reflected beam from each depth of the measuring object S interferes with the reference beam with various optical path length differences, the light intensity I(k) detected by the interference beam detection means 40 may be expressed in the following.

$$I(k) = \int_0^\infty S(l)[1 + \cos(kl)]\,dl \quad (1)$$

where, k is the wave number, l is the optical path length difference between the reference beam and reflected beam. Formula (1) above may be regarded as an interferogram in the optical frequency domain with the wave number k as a parameter. Accordingly, a tomographic image may be generated by determining the light intensity S(l) of the interference signal ISO in each wavelength by performing, frequency analyses, through Fourier transforms, on the spectral interference patterns detected by the interference beam detection means 40a, 40b, 40c, and 40d in the tomographic image processing means 50, and obtaining distance information from the measurement start position and tomographic information.

Next, an example operation of the optical tomographic imaging apparatus 1 will be described. As illustrated in FIG. 4, the light beams La, Lc, and the light beams Lb, Ld are respectively swept in wavelength and alternately outputted from the light source unit 10 on the basis of each sweep period. First, the operation for outputting the light beams La, Lc will be described. It is noted that the light beams shown in FIG. 2 are those when the light beams La, Lc are outputted.

As illustrated in FIG. 2, the light beams La, Lc outputted from the light source unit 10 and guided through the optical fiber FB1 are inputted to the beam splitting means 3. In the beam combining means 3, the light beam La is split into a measuring beam L1a and a reference beam L2a, and the light beam Lc is split into a measuring beam L1c and a reference beam L2c. The measuring beams L1a, L1c are guided through the optical fiber FB2, passed through the circulator 5, guided by the optical fiber FB4, inputted to the probe 30 through the optical rotary connector 31, which are then guided by the probe 30 and irradiated onto the measuring object S. Then, reflected beams L3a, L3c from each depth position "z" of the measuring object S are guided by the probe 30 and optical fiber FB4, passed through the circulator 5, guided by the optical fiber FB5, and inputted to the reflected beam separation means 86.

The reflected beam separation means 86 is synchronized by the external trigger, and the light beams inputted to the reflected beam separation means 86 are outputted to the optical fiber FB6a while the light beams La, Lc are outputted from the light source unit 10, and to the optical fiber FB6b while the light beams Lb, Ld are outputted from the light source unit 10. Accordingly, the reflected beams L3a, L3c are guided by the optical fiber FB6a and inputted to the reflected beam separation means 85a.

The reflected beam separation means 85a outputs the reflected beam L3a in the same wavelength range as that of the light beam La to the optical fiber FB8a, and the reflected beam L3c in the same wavelength range as that of the light beam Lc to the optical fiber FB8c. The beam combining means 4a is connected to the optical fiber FB8a, and the beam combining means 4c is connected to the optical fiber FB8c.

In the mean time, the reference beams L2a, L2c split by the beam splitting means 3 are guided through the optical fiber FB3, and inputted to the reference beam separation means 76 after the optical path length thereof is controlled by the optical path length control means 20 provided in the middle of the optical fiber FB3.

The reference beam separation means 76 is synchronized by the external trigger, and the reference beams inputted to the reference beam separation means 76 are outputted to the optical fiber FB7a while the light beams La, Lc are outputted from the light source unit 10, and to the optical fiber FB7b while the light beams Lb, Ld are outputted from the light source unit 10. Accordingly, the reflected beams L2a, L2c are guided by the optical fiber FB7a and inputted to the reflected beam separation means 75a.

The reference beam separation means 75a outputs the reference beam L2a in the same wavelength range as that of the light beam La to the optical fiber FB9a, and the reflected beam L3c in the same wavelength range as that of the light beam Lc to the optical fiber FB9c. The beam combining means 4a is connected to the optical fiber FB9a, and the beam combining means 4c is connected to the optical fiber FB9c.

In the beam combining means 4a, the reflected beam L3a and reference beam L2a are combined together, and the interference beam L4a produced thereby is divided into halves and outputted to the interference beam detection means 40a. In the interference beam detection means 40a, the interference beam L4a is detected through balanced detection and photoelectrically converted to generate the interference signal ISa, which is outputted to the tomographic image processing means 50.

In the beam combining means 4c, the reflected beam L3c and reference beam L2c are combined together, and the interference beam L4c produced thereby is divided into halves and outputted to the interference beam detection means 40c. In the interference beam detection means 40c, the interference beam L4c is detected through balanced detection and photoelectrically converted to generate the interference signal ISc, which is outputted to the tomographic image processing means 50.

After the light beams La, Lc are swept for a single period, the light beams Lb, Ld are outputted from the light source unit 10. The operation while the light beams Lb, Ld are outputted from the light source unit 10 is identical to the operation while the light beams La, Lc are outputted from the light source unit 10 up to the input operation to the reflected beam separation means 86 and reference beam separation means 76.

In the reflected beam separation means 86, the reflected beams based on the light beams Lb, Ld respectively are guided by the optical fiber FB6b and inputted to the reflected beam separation means 85b. The reflected beam separation means 85b outputs the reflected beam L3b based on the light beam Lb to the optical fiber FB8b, and the reflected beam L3d based on the light beam Ld to the optical fiber FB8d. The beam combining means 4b is connected to the optical fiber FB8b, and the beam combining means 4d is connected to the optical fiber FB8d.

Further, in the reference beam separation means 76, the reference beams L2b, L2d based on the light beams Lb, Ld respectively are guided through the optical fiber FB 7b and inputted to the reference beam separation means 75b. The reference beam separation means 75b outputs the reference beam L2b based on the light beam Lb to the optical fiber FB9b, and the reference beam L2d based on the light beam Ld to the optical fiber FB9d. The beam combining means 4b is connected to the optical fiber FB9b, and the beam combining means 4d is connected to the optical fiber FB9d.

In the beam combining mean 4b, the reflected beam L3b and reference beam L2b which are based on the light beam Lb are combined together, and the interference beam L4b produced thereby is divided into halves and outputted to the interference beam detection means 40b. In the interference beam detection means 40b, the interference beam L4b based on the light beam Lb is detected through balanced detection and photoelectrically converted to generate the interference signal ISb, which is outputted to the tomographic image processing means 50.

In the beam combining mean 4d, the reflected beam L3d and reference beam L2d which are based on the light beam Lb are combined together, and the interference beam L4d produced thereby is divided into halves and outputted to the interference beam detection means 40d. In the interference beam detection means 40d, the interference beam L4d based on the light beam Ld is detected through balanced detection and photoelectrically converted to generate the interference signal ISd, which is outputted to the tomographic image processing means 50.

In the tomographic image processing means 50, a two-dimensional tomographic image is generated by calculating tomographic information at each depth position using the interference signal ISO obtained from the interference signals ISa, ISb, ISc, and ISd in the manner as described above. The generated tomographic image is displayed on the display unit 60 which includes a CRT (Cathode Ray Tube), a liquid crystal display, or the like.

As described above, according to the optical tomographic imaging apparatus 1, a plurality of light beams having different wavelengths is irradiated on the measuring object S at the same time, and a plurality of interference beams produced thereby is detected with respect to each light beam, thereby a high resolution image may be obtained rapidly. In particular, light beams having separate wavelength ranges with each other are outputted during the same time period, and light beams having partially overlapping wavelength ranges with each other are outputted during different time periods by the control means 16. This allows the use of beam splitting means having wavelength selectivity and separation of the reference and reflected beams with respect to each light beam depending on the time, so that the problem of signal mixing in the detector encountered when combining beams in the past may be solved.

Further, the optical tomographic imaging apparatus 1 includes an interference beam detection means for each light beam, so that each interference beam detection means may be optimized in the structure according to the wavelength range of each light beam, thereby the detection accuracy thereof may be enhanced and the resolution of a tomographic image may be improved. Further, the component parts used in the interference beam detection means need only to cover the wavelength range of each light beam. This may relax the restrictions on the component parts to be used in comparison with the past and allow the use of general purpose component parts, so that the apparatus may be constructed easily.

In the optical tomographic imaging apparatus 1 according to the first embodiment, the description has been made of a case in which a continuous spectrum is formed by all of the light beams outputted from the light source unit 10. The present invention is not limited to this, and the spectrum formed by all of the light beams outputted from the light source unit 10 may be discontinuous as will be described in a second embodiment hereinbelow.

Figure 5:
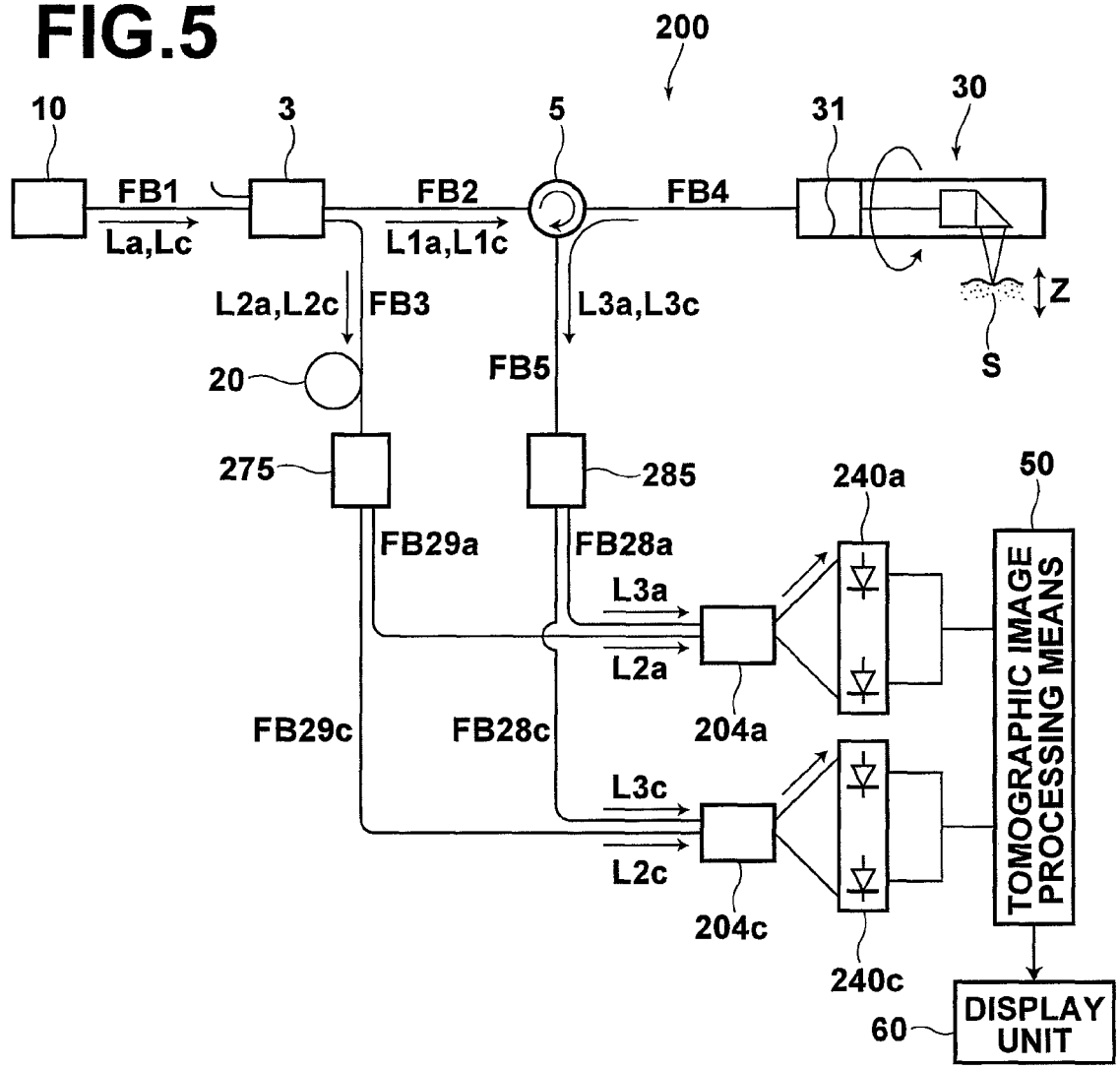
FIG. 5 is a schematic configuration diagram of the optical tomographic imaging apparatus according to a second embodiment of the present invention.

Next, the optical tomographic imaging apparatus 200 according to a second embodiment of the present invention will be described with reference to FIG. 5. FIG. 5 is a schematic configuration diagram of the optical tomographic imaging apparatus 200. The optical tomographic imaging apparatus 200 differs from the optical tomographic imaging apparatus 1 shown in FIG. 2, in the spectrum formed by all of the light beams outputted from the light source unit 10 and in the structures of the reference beam separation means and reflected beam separation means. Further, in the optical tomographic imaging apparatus 200, the processing performed in the tomographic image processing means 50 is different from that of the first embodiment. Hereinafter, the description will be focused mainly on the differences, and in the optical tomographic imaging apparatus 200 shown in FIG. 5, components identical to those of the optical tomographic imaging apparatus 1 shown in FIG. 2 are given the same reference symbols and will not be elaborated upon further here.

Figure 6:
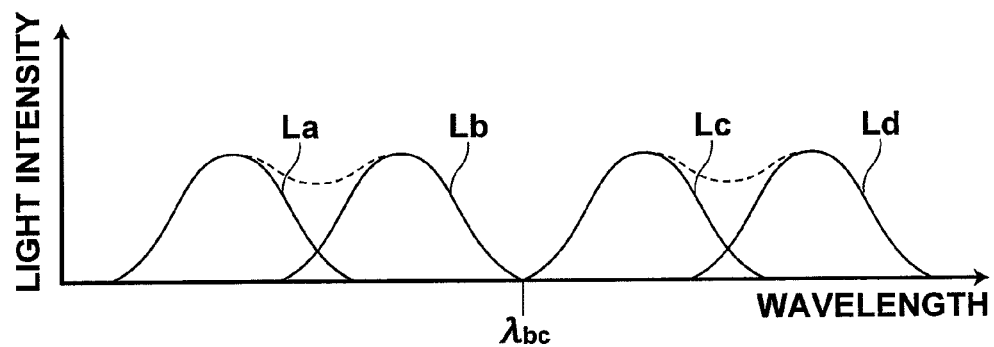
FIG. 6 illustrates respective spectra of light beams outputted from the light source unit according to a second embodiment of the present invention.

In the present embodiment, a wavelength $\lambda bc$ where the light intensity falls below or to about −10 dB with respect the peak light intensity appears between the peak wavelengths of the light beams Lb, Lc, and thereby the wavelengths of the light beams Lb, Lc are separated, as illustrated in FIG. 6. Thus, the spectrum formed by all of the light beams outputted from the light source unit 10 is discontinuous.

The light beams outputted from the light source unit 10 are identical to those of the first embodiment other than the point described above, and the light beams La, Lb, Lc, and Ld are swept in wavelength at a constant period, have different wavelength ranges with each other, have a continuous spectrum within the respective wavelength ranges, portions of the wavelength ranges of the light beams La, Lb are overlapping with each other, and portions of the wavelength ranges of the light beams Lc, Ld are overlapping with each other.

In addition, all of the light sources and control means 16 are synchronized by a not shown external trigger, and the light beams La, Lc, and the light beams Lb, Ld are respectively swept in wavelength and alternately outputted from the light source unit 10 on the basis of each sweep period.

In the optical tomographic imaging apparatus shown in FIG. 5, a reference beam separation means 275 is employed instead of the reference beam separation means 76, 75a, and 75b employed in the optical tomographic imaging apparatus 1 shown in FIG. 2, and a reflected beam separation means 285 is employed instead of the reflected beam separation means 86, 85a, and 85b.

Each of the reference beam separation means 275 and reflected beam separation means 285 has a function to separate light beams according to a predetermined cutoff wavelength, and is formed of, for example, a WDM coupler. The cutoff wavelengths of the reference beam separation means 275 and reflected beam separation means 285 are set at the wavelength $\lambda bc$. This allows light beams based on the light beams Lb, Lc to be separated efficiently.

The optical tomographic imaging apparatus 200 includes beam combining means 204a, 204c and interference beam detection means 240a, 240c. The beam combining means 204a and interference beam detection means 240a are structured to accept wavelengths of the light beams La, Lb, and the beam combining means 204b and interference beam detection means 240b are structured to accept wavelengths of the light beams Lc, Ld. As described above, the beam combining means and interference beam detection means of the optical tomographic imaging apparatus 200 differ from the beam combining means and interference beam detection means of the optical tomographic imaging apparatus 1 only in acceptable wavelength range, and the other basic structures and functions are identical.

An example operation of the optical tomographic imaging apparatus 200 shown in FIG. 5 will now be described. The operation when the light beams La, Lc are outputted from the light source unit 10 will be described first. The process from outputting the light beams La, Lc from the light source unit 10, splitting them into the measuring beams L1a, L1b and reference beams L2a, L2c to guiding the reflected beams L3a, L3c through the optical fiber FB5, and the process of guiding the reference beams L2a, L2c through the optical fiber FB3 are identical to those of the first embodiment.

Thereafter, the reflected beams L3a, L3c guided through the optical fiber FB5 are inputted to the reflected beam separation means 285 and separated from each other therein. The reflected beam L3a is outputted to the optical fiber FB28a and inputted to the beam combining means 204a, while the reflected beam L3c is outputted to the optical fiber FB28c and inputted to the beam combining means 204c.

In the mean time, the reference beams L2a, L2c guided through the optical fiber FB3 are inputted to the reference beam separation means 275 and separated from each other therein. The reference beam L2a is outputted to the optical fiber FB 29a and inputted to the beam combining means 204a, while the reference beam L2c is outputted to the optical fiber FB 29c and inputted to the beam combining means 204c.

In the beam combining means 204a, the reflected beam L3a is combined with the reference beam L2a, and the interference beam L4a produced thereby is divided into halves and outputted to the interference beam detection means 240a. In the beam combining means 204c, the reflected beam L3c is combined with the reference beam L2c, and the interference beam L4c produced thereby is divided into halves and outputted to the interference beam detection means 240c. In the interference beam detection means 240a, 240c, the interference beams L4a, L4c are detected through balanced detection and photoelectrically converted, and thereby the interference signals ISa, ISb are generated and outputted to the tomographic image processing means 50.

The operation process when the light beams Lb, Ld are outputted from the light source unit 10 is identical to that when the light beams La, Lc are outputted from the light source unit 10 described above.

Figure 7:
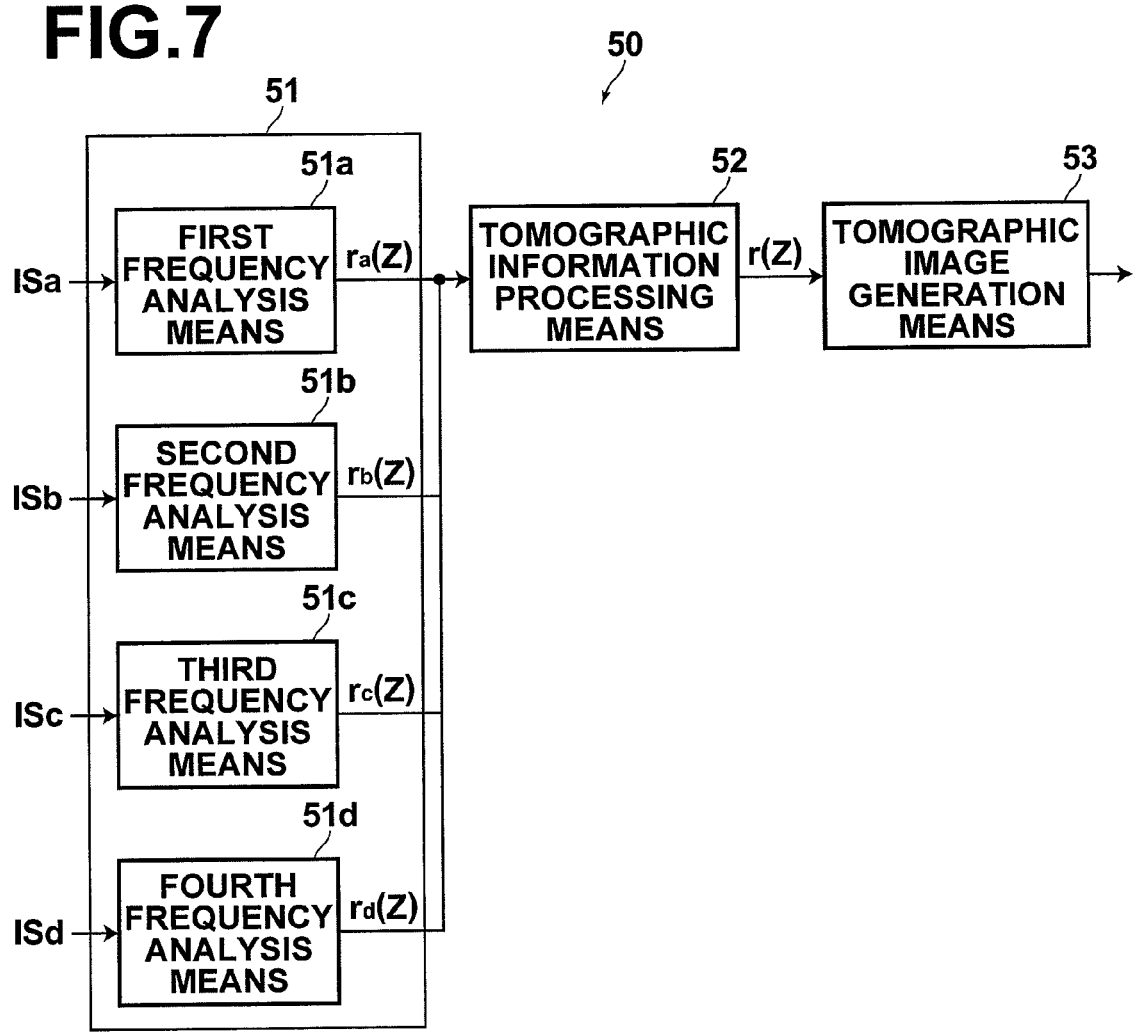
FIG. 7 is a block diagram illustrating an example of the tomographic image processing means shown in FIG. 5.

Now, the structure and operation of the tomographic image processing means 50 according to the second embodiment will be described. The tomographic image processing means 50 includes, for example, a computer system such as a personal computer. The tomographic image processing means 50 has functions to detect a plurality of intermediate tomographic information (reflectivities) ra(z), rb(z), rc(z), rd(z) at each dept position of the measuring object S by performing frequency analyses on the interference signals ISa, ISb, ISc, ISd photoelectrically converted by the interference beam detection means 40, and to obtain a tomographic image of the measuring object using the plurality of intermediate tomographic information ra(z), rb(z), rc(z), rd(z). More specifically, as illustrated in FIG. 7, the tomographic image processing means 50 includes a frequency analysis means 51 that performs frequency analyses on the plurality of interference beams ISa, ISb, ISc, ISd to detect the intermediate tomographic information ra(z), rb(z), rc(z), rd(z) at each depth position; a tomographic information processing means 52 that generates tomographic information r (z) from the plurality of intermediate tomographic information ra (z), rb (z), rc(z), rd(z) detected by the frequency analysis means 51; and a tomographic image generation means 53 that generates a tomographic image using the tomographic information r(z) generated by the tomographic information processing means 52.

The frequency analysis means 51 includes a first frequency analysis means 51a that performs a frequency analysis on the interference signal ISa to detect the intermediate tomographic information ra(z) which is based on the light beams La, a second frequency analysis means 51b that performs a frequency analysis on the interference signal ISb to detect the intermediate tomographic information rb(z) which is based on the light beams Lb, a third frequency analysis means 51c that performs a frequency analysis on the interference signal ISc to detect the intermediate tomographic information rc(z) which is based on the light beams Lc, and a fourth frequency analysis means 51d that performs a frequency analysis on the interference signal ISd to detect the intermediate tomographic information rd(z) which is based on the light beams Ld.

Here, a method for calculating the intermediate tomographic information (reflectivity) ra(z) in the first frequency analysis means 51a based on the interference signal ISa will be described briefly. For more detailed description, reference is made to the literature by M. Takeda, "Optical Frequency Scanning Interference Microscopes", Optics Engineering Contact, Vol. 41, No. 7 pp. 426-432, 2003.

Figure 8:
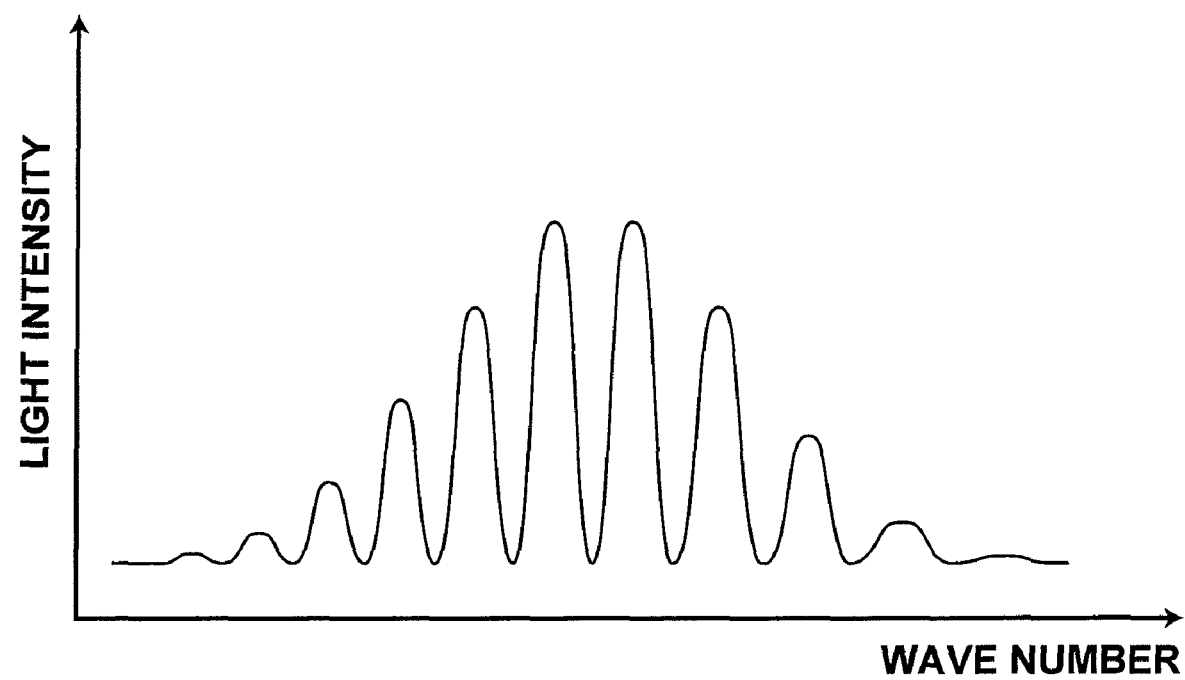
FIG. 8 is a graph illustrating an example interference beam detected by the interference beam detection means shown in FIG. 5.
Figure 9:
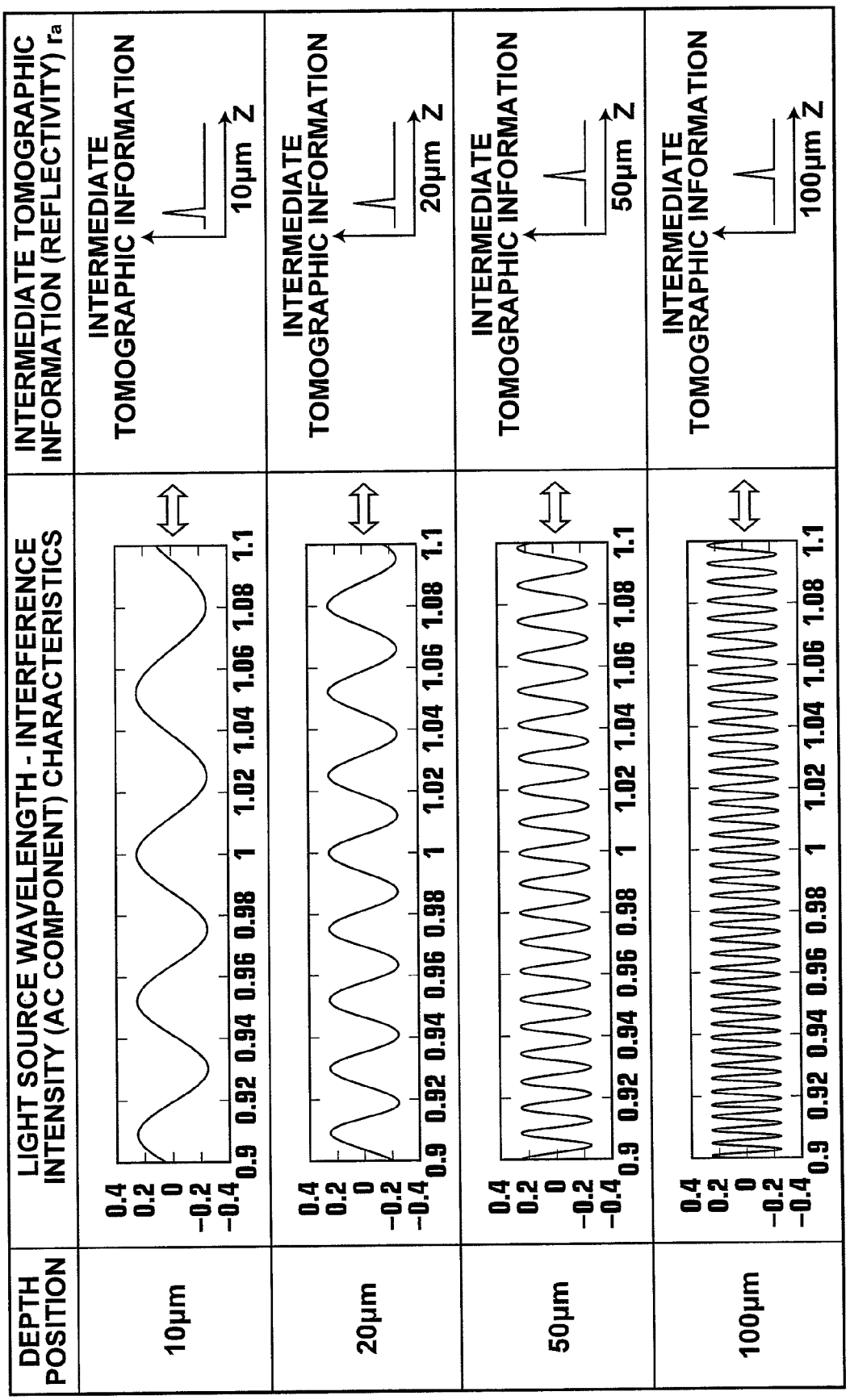
FIG. 9 illustrates tomographic information at each depth position obtained by frequency analyzing an interference beam detected by the interference beam detection means shown in FIG. 5.

Assuming the light intensity of the interference pattern with respect to each optical path length difference l to be S(l) when the measuring beam is irradiated onto the measuring object S, and reflected beam from each depth of the measuring object interferes with the reference beam with various optical path length differences (dept positions of the measuring object S), the light intensity I(k) detected by the interference beam detection means 40 may be expressed in the following and represented, for example, by the graph illustrated in FIG. 8.

$$I(k) = \int_0^\infty S(l)[1 + \cos(kl)]\,dl \tag{1}$$

where, k is the wave number, l is the optical path length difference between the reference beam and reflected beam. Formula (1) above may be regarded as an interferogram in the optical frequency domain with the wave number k as a parameter. Accordingly, the light intensity S(l) of the interference signal ISa in each wavelength may be determined by performing, in the frequency analysis means 51, a frequency analysis, through Fourier transform, on the spectral interference pattern detected by the interference beam detection means 40, thereby the reflectivity at each depth position may be obtained, as illustrated in FIG. 9. Then, information of the distance from the measurement start position and the intermediate tomographic information ra(z) are obtained.

Likewise, the second frequency analysis means 51b obtains information of the distance from the measurement start position and the intermediate tomographic information rb (z). The third frequency analysis means 51c obtains information of the distance from the measurement start position and the intermediate tomographic information rc(z), and the fourth frequency analysis means 51d obtains information of the distance from the measurement start position and the intermediate tomographic information rd(z). That is, the plurality of intermediate tomographic information ra(z), rb (z), rc(z), rd(z) are obtained from the same beam-irradiated region of the measuring object S in the frequency analysis means 51.

Figure 10:
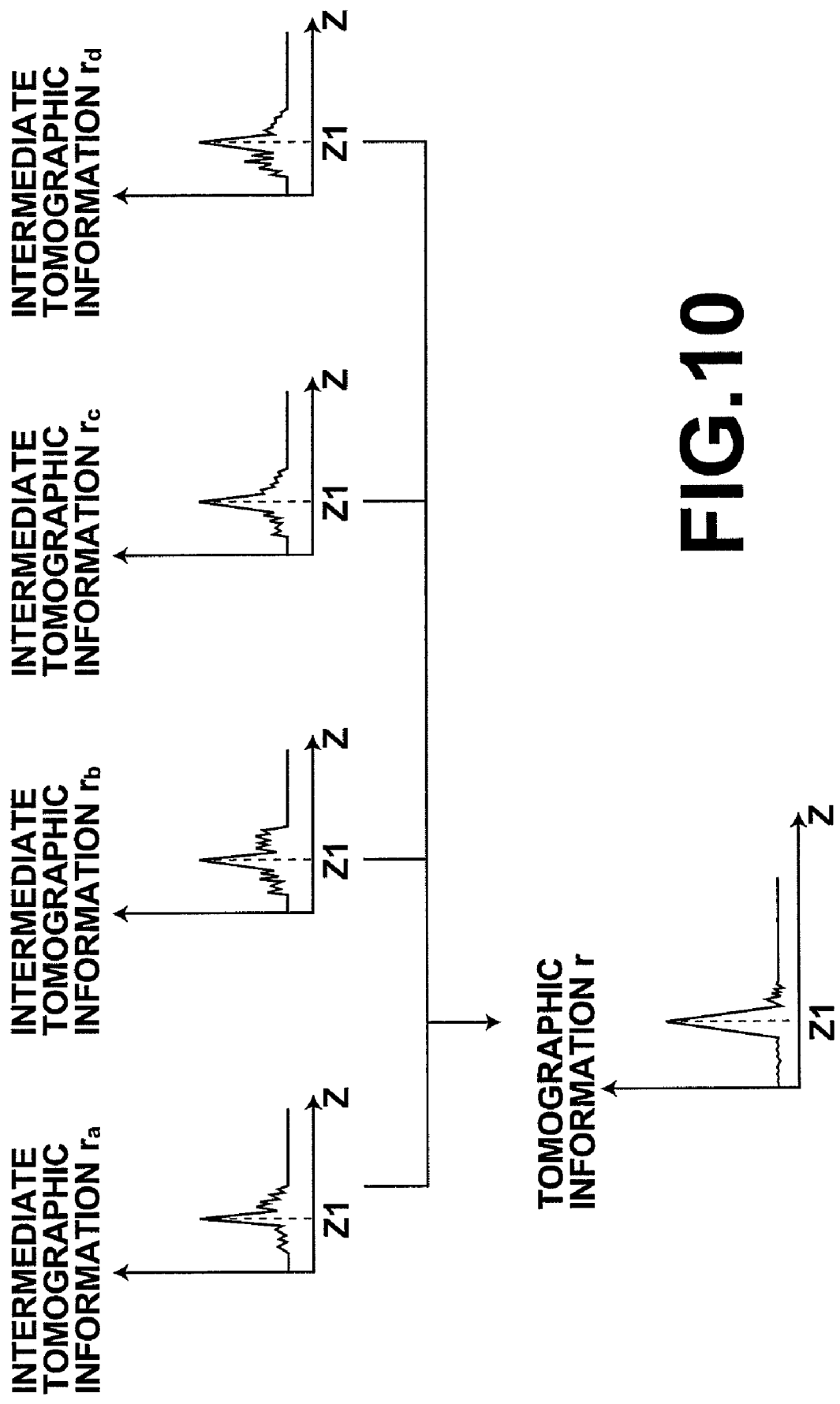
FIG. 10 illustrates how the tomographic information used for generating a tomographic image is generated from a plurality of sets of tomographic information in the tomographic image processing means shown in FIG. 5.

Then, intermediate tomographic information ra(z), rb(z), rc(z), rd(z) are combined in consideration of the wavelength ranges in which the respective interference signals are obtained using spectral information of the light sources, thereby the resolution of the tomographic information r(z) may be increased. FIG. 10 conceptually illustrates this idea. The ra(z), rb(z), rc(z), rd(z) obtained by Fourier transform of the interference signals ISa, ISb, ISc, ISd, true tomographic information r(z), and Fourier transforms ha(z), hb(z), hc(z), hd(z) of the spectral shapes of the light beams La, Lb, Lc, Ld are in the following relationship.

$$ra(z) = r(z) \otimes ha(z) \quad (2)$$

$$rb(z) = r(z) \otimes hb(z) \quad (3)$$

$$rc(z) = r(z) \otimes hc(z) \quad (4)$$

$$rd(z) = r(z) \otimes hd(z) \quad (5)$$

$\otimes$ denotes convolution operation

These may be deployed to $ra = [ra(0), ra(1 \times dza), \text{- - -}]^T$, $rb = [rb(0), rb(1 \times dzb), \text{- - -}]^T$, $rc = [rc(0), rc(1 \times dz), \text{- - -}]^T$, $rd = [rd(0), rd(1 \times dz), \text{- - -}]^T$, $r = [r(0), r(1 \times dz), \text{- - -}]^T$, and expressed in discrete representations, then $$Ha \cdot r = ra \quad (6)$$

$$Hb \cdot r = rb \quad (7)$$

$$Hc \cdot r = rc \quad (8)$$

$$Hd \cdot r = rd \quad (9)$$

where, Ha, Hb, Hc, Hd are matrices formed of each vector of $ha = [ha(0), ha(1 \times dz), \text{- - -}]$, $hb = [hb(0), hb(1 \times dz), \text{- - -}]$, $hc = [hc(0), hc(1 \times dz), \text{- - -}]$, and $hd = [hd(0), hd(1 \times dz), \text{- - -}]$ arranged by displacing the element thereof. Through a known method, such as iteration method, the tomographic information "r" may be obtained as the optimum solution of the relational expressions.

As described above, by calculating the tomographic information r(z) from the relational expressions in consideration of the difference in wavelength among the light beams La, Lb, Lc, Ld outputted from the light source unit 10, the tomographic information r (z) may be calculated more accurately, thereby a high resolution tomographic image may be generated. It is noted that this method is also applicable to the first embodiment.

In the present embodiment, the wavelength ranges of the light beams Lb, Lc are separated, and the cutoff wavelengths of the reflected beam separation means 285 and reference beam separation means 275 are set at the wavelength λbc. This may reduce the number of separation means, beam combining means, and interference beam detection means in comparison with the first embodiment, so that the structure of the apparatus may be simplified, allowing downsizing and cost reductions of the apparatus.

It is noted that, in the optical tomographic imaging apparatus 200 according to the second embodiment, beam combining means 15a, 15b of the light source unit 10 may be those which are identical to those of the optical tomographic imaging apparatus 1, those which are identical to the reflected beam separation means 285 and reference beam separation means 275 having the cutoff wavelength set at the wavelength λbc, or those optimized in consideration of the spectrum of each light source.

The optical tomographic imaging apparatus 200 according to the second embodiment is advantageous when the light beams Lb, Lc have separated wavelength ranges, since it may perform measurement with high light utilization efficiency, but the apparatus is also applicable to the case in which each of the light beams outputted from the light source unit 10 has a spectrum like that shown in FIG. 3A, though the light utilization efficiency is degraded. In this case, it is preferable that the cutoff wavelengths of the reflected beam separation means 285 and reference beam separation means 275 are set at the wavelength where the spectra of the light beams Lb and Lc intersect with each other.

Next, the optical tomographic imaging apparatus according to a third embodiment will be described with reference to FIG. 11. The optical tomographic imaging apparatus according to the third embodiment differs from the optical tomographic imaging apparatus 200 according to the second embodiment only in the structure of the light source unit. Therefore, only the light source unit will be described in the third embodiment, and other components will not be elaborated upon further here. In addition, in FIG. 11, components identical to those of the light source unit 10 shown in FIG. 1 are given the same reference symbols, and will not be elaborated upon further here.

Figure 11:
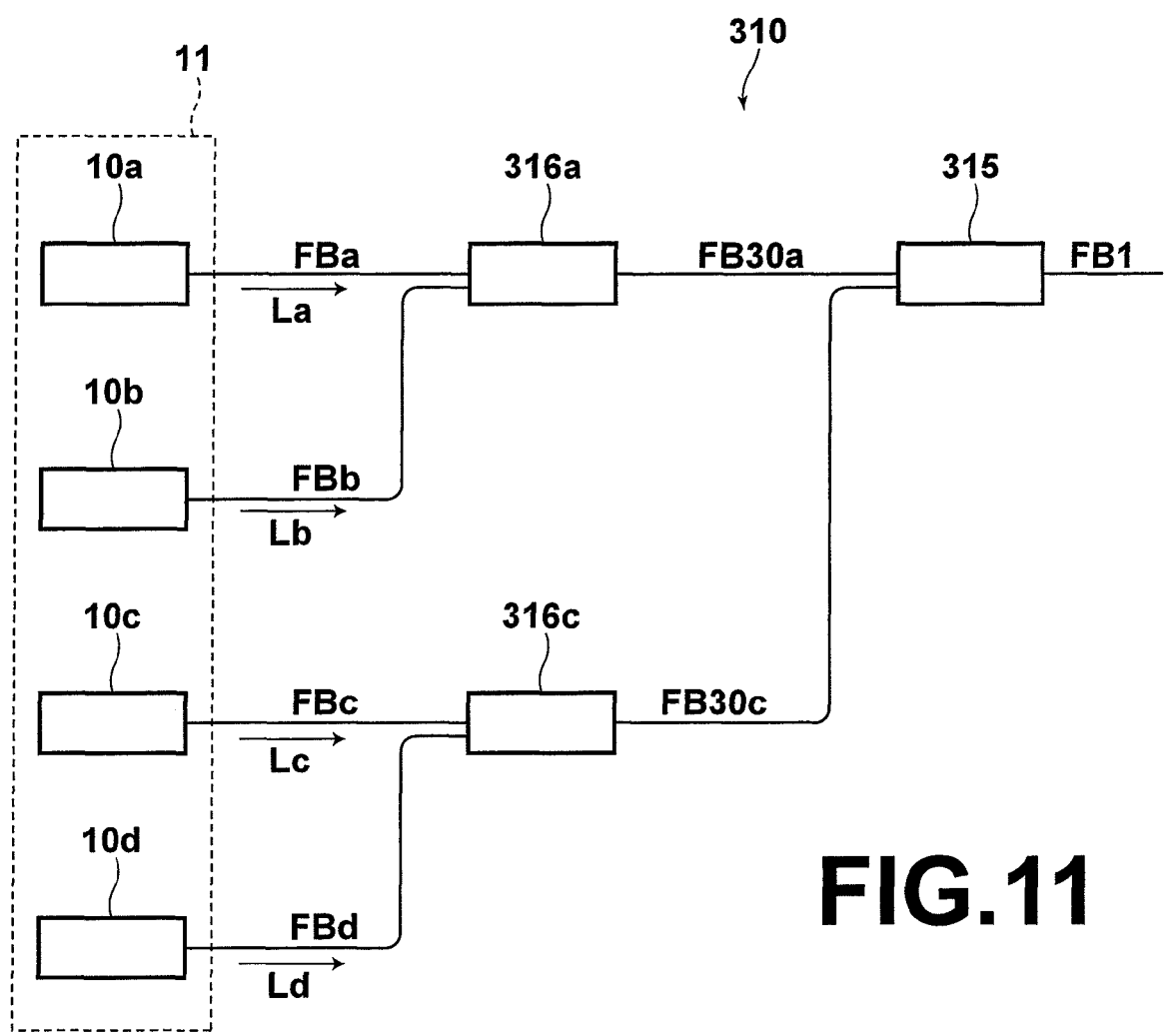
FIG. 11 is a schematic configuration diagram of the light source unit according to a third embodiment of the present invention.

FIG. 11 is a schematic configuration diagram of a light source unit 310 included in the optical tomographic imaging apparatus according to the third embodiment. The light source unit 310 is a unit that combines and outputs a plurality of light beams, having the function of the light control means of the present invention. The light source unit 310 includes: a light emission section 11, a beam combining means 315 which is a wavelength combining means having a wavelength selectivity, that combines and outputs at least two of the light beams which the light emission section 11 is capable of outputting; control means 316a, 316c located upstream of the beam combining means 315 in the optical paths of the light beams and perform control such that at least one light beam is outputted at a time period which is different from a time period in which another one or more light beams are outputted, thereby causing two or more light beams having different wavelengths with each other are combined and outputted at the same time. That is, it is one of the characteristic features of the light source unit 310 that the control means is disposed upstream of the beam combining means in comparison with the light source unit 10.

In the third embodiment, it is noted that the spectrum of each of the light beams La, Lb, Lc, Ld outputted from the light emission section 11 is identical to that shown in FIG. 6, and the wavelength ranges of the light beams Lb, Lc are separated with each other.

As illustrated in FIG. 11, the output terminals of the light sources 10a, 10b are linked to the input terminals of the control means 316a through optical fibers FBa, FBb respectively, and the output terminals of the light sources 10c, 10d are linked to the input terminals of the control means 316c through optical fibers FBc, FBd respectively.

In the present embodiment, each of the control means 316a, 316b has two input terminals and one output terminal, but it may have more input or output terminals. The output terminals of the control means 316a, 316c are linked to the two input terminals of the beam combining means 315 through optical fibers FB30a, FB30c respectively. An optical fiber FB1 is connected to the output terminal of the beam combining means 315.

Each of the control means 316a, 316c is formed of, for example, a switching element, and has a function to output only the light beam inputted from either one of the two input terminals and to block the light beam inputted from the other input terminal, thereby switching the light beams according to the time. The control means 316a, 316c also cause light beams having separate wavelength ranges with each other to be outputted from the light source unit 310 during the same time period, and light beams having partially overlapping wavelength ranges to be outputted from the light source unit 310 during different time periods.

The beam combining means 315 has a function to combine light beams according to a predetermined cutoff wavelength, and is formed of, for example, a WDM coupler. The cutoff wavelength of the beam combining means 315 is set to the $\lambda bc$.

The number of combinations of light beams which may be outputted from the light source unit 310 of the present embodiment at the same time is four: combination of light beams La and Lc, combination of light beams La and Ld, combination of light beams Lb and Lc, and combination of light beams Lb and Ld. As described above, the wavelength ranges of the light beams Lb, Lc are separated from each other, so that the wavelength ranges of a plurality of light beams irradiated on the measuring object S are invariably separated from each other without synchronizing the control means 316a, 316c in the third embodiment. Accordingly, also in the third embodiment, it is possible for the reflected beam separation means 285 and the reference beam separation means 275 to separate the light beams from each other, thereby the problem of signal mixing in the detector may be solved and rapid high resolution measurement is allowed.

Where each of the light beams outputted from the light source unit 310 has a spectrum like that shown in FIG. 3A, it is noted that the light source unit 10 may be synchronized by the control means 316a, 316b such that the light beams Lb, Lc are not outputted at the same time.

Next, the optical tomographic imaging apparatus according to a fourth embodiment will be described with reference to FIG. 12. The optical tomographic imaging apparatus according to the fourth embodiment differs from the optical tomographic imaging apparatus 1 according to the first embodiment only in the structure of the light source unit. Therefore, only the light source unit will be described in the fourth embodiment, and other components will not be elaborated upon further here. In addition, in FIG. 12, components identical to those of the light source unit 10 shown in FIG. 1 are given the same reference symbols, and will not be elaborated upon further here.

Figure 12:
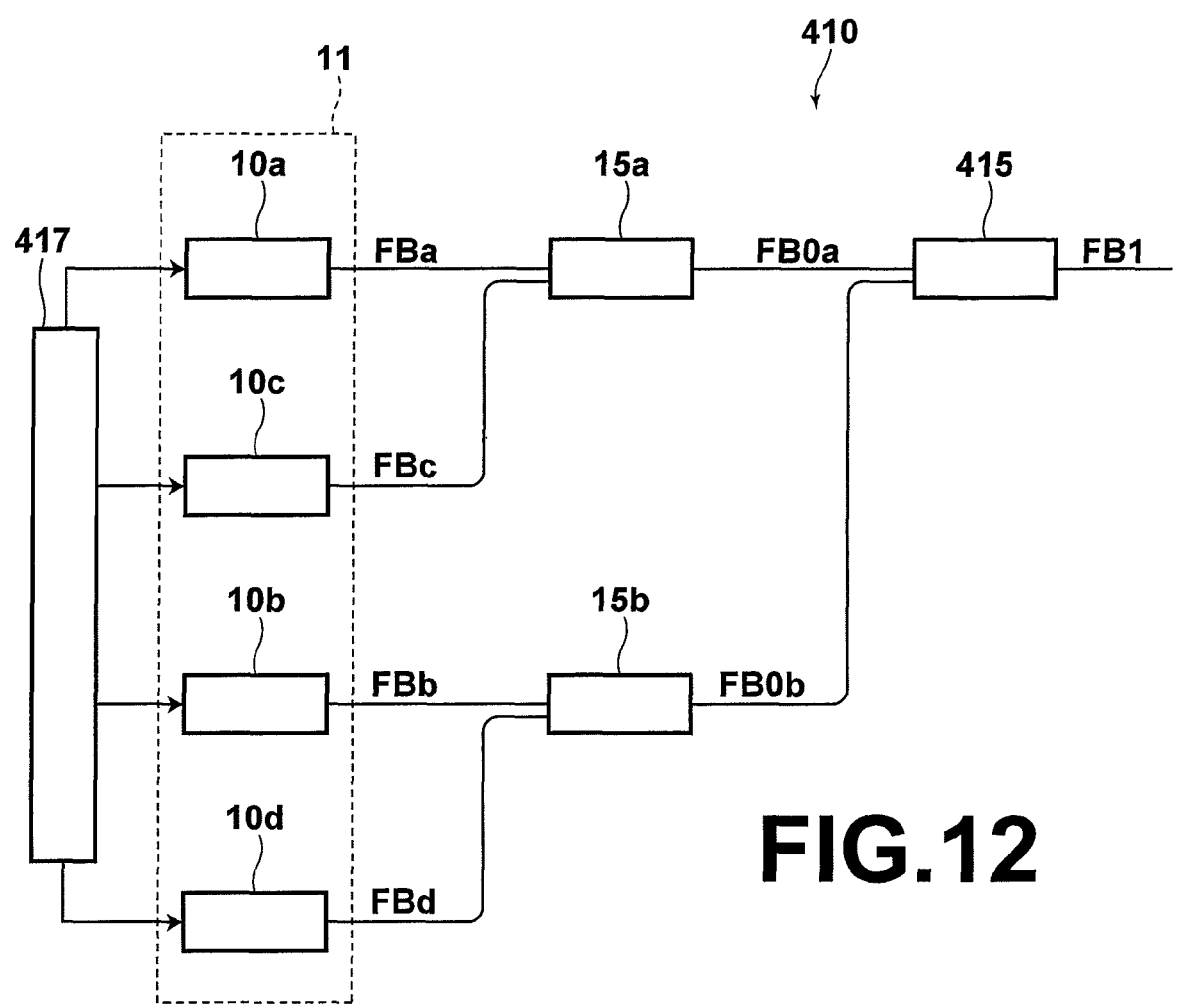
FIG. 12 is a schematic configuration diagram of the light source unit according to a fourth embodiment of the present invention.

FIG. 12 is a schematic configuration diagram of a light source unit 410 included in the optical tomographic imaging apparatus according to the fourth embodiment. The light source unit 410 is a unit that combines and outputs a plurality of light beams, having the function of the light control means of the present invention. The light source unit 410 is characterized in that it replaces the control means 16 with a beam combining means 415 and further includes a control means 417 in comparison with the light source unit 10 shown in FIG. 1.

The beam combining means 415 is formed of, for example, a 2×1 optical fiber coupler with a branching ratio of 50:50.

The control means 417 individually controls emission/extinction (ON/OFF) of the light sources 10a, 10b, 10c, and 10d. The control means 417 causes light beams having separate wavelength ranges with each other to be outputted from the light source unit 410 during the same time period, and light beams having partially overlapping wavelength ranges with each other to be outputted from the light source unit 410 during different time periods.

The control means 417 may provide the same combinations of the light beams outputted from the light source unit 410 as in the first embodiment, thereby the problem of signal mixing when a plurality of light beams having different wavelengths is outputted may be solved as in the first embodiment.

Figure 13:
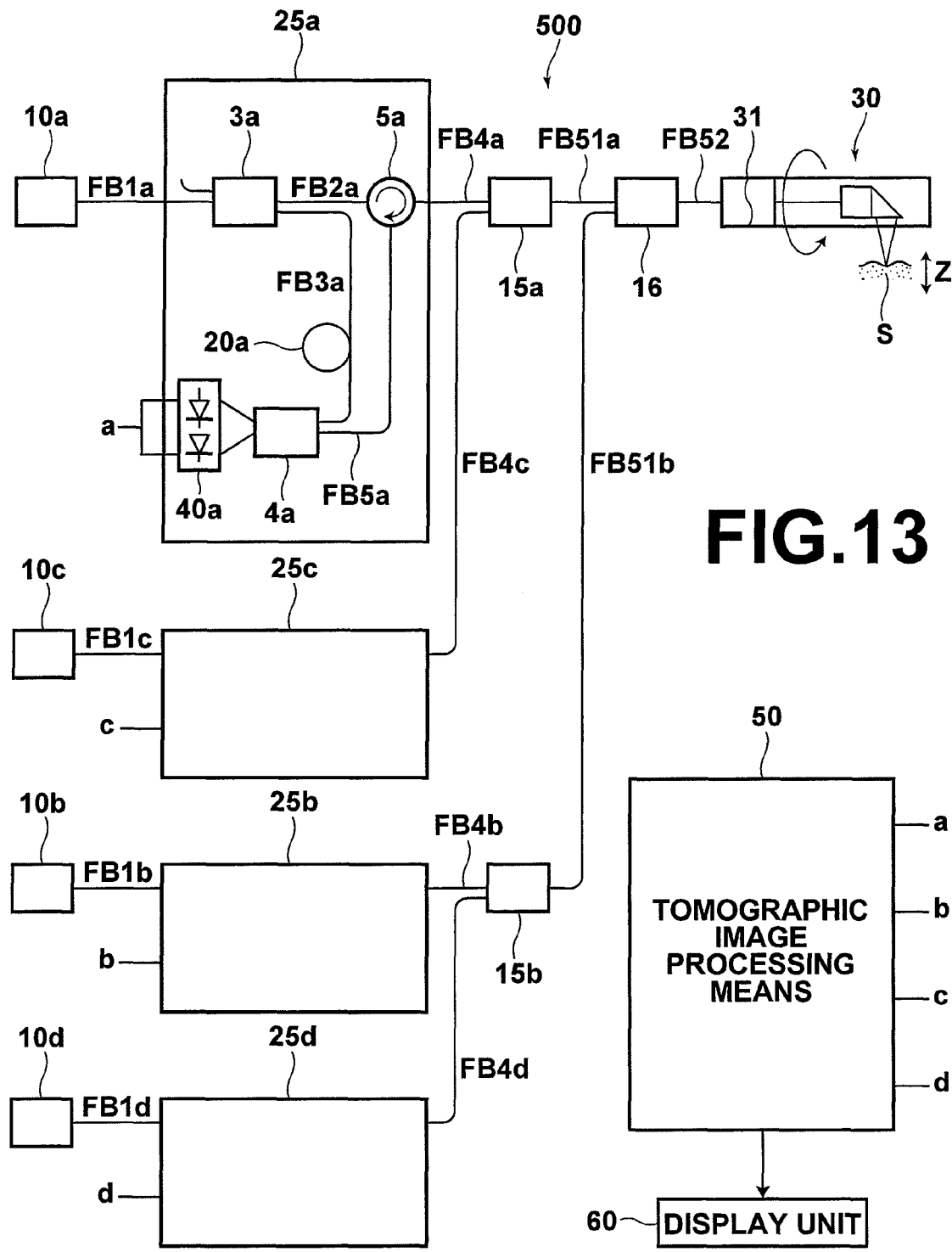
FIG. 13 is a schematic configuration diagram of the optical tomographic imaging apparatus according to a fifth embodiment of the present invention.

Next, the optical tomographic imaging apparatus 500 according to a fifth embodiment will be described with reference to FIG. 13. The optical tomographic imaging apparatus 500 basically differs from the optical tomographic imaging apparatus 1 shown in FIG. 2 in that the beam combining means 15a, 15b and control means 16 are disposed downstream of interferometers, and an interferometer is provided for each light beam. Hereinafter, the description will be focused mainly on the differences, and in the optical tomographic imaging apparatus 500 shown in FIG. 13, components identical to those of the optical tomographic imaging apparatus 1 shown in FIG. 2 are given the same reference symbols and will not be elaborated upon further here.

The optical tomographic imaging apparatus 500 includes light sources 10a, 10b, 10c, and 10d, interferometer units 25a, 25b, 25c, and 25d provided for the light sources 10a, 10b, 10c, and 10d respectively, beam combining means 15a, 15b, a control means 16, a probe 30, and a tomographic image processing means 50.

The light source 10a is linked to the interferometer unit 25a through an optical fiber FB1a, and the interferometer unit 25a is linked to one end of the beam combining means 15a through an optical fiber FB4a. Likewise, the light source 10c is linked to the interferometer unit 25c through an optical fiber FB1c, and the interferometer unit 25c is linked to one end of the beam combining means 15a through an optical fiber FB4c.

The light source 10b is linked to the interferometer unit 25b through an optical fiber FB1b, and the interferometer unit 25b is linked to one end of the beam combining means 15b through an optical fiber FB4b. Likewise, the light source 10d is linked to the interferometer unit 25d through an optical fiber FB1d, and the interferometer unit 25d is linked to one end of the beam combining means 15b through an optical fiber FB4d.

The other end of the beam combining means 15a is linked to one end of the control means 16 by an optical fiber FB51a, and the other end of the beam combining means 15b is linked to one end of the control means 16 by an optical fiber FB51b. The other end of the control means 16 is linked to an optical rotary connector 31 by an optical fiber FB52.

Each of the interferometer units 25a, 25b, 25c, and 25d is linked to the tomographic image processing means 50. Basically, the interferometer units 25a, 25b, 25c, and 25d have an identical structure except that the wavelength ranges of input light beams are different from each other. Therefore, FIG. 13 illustrates the structure of the interferometer unit 25a only, and the structures of the interferometer units 25b, 25c, and 25d are omitted in order to avoid complications.

The structure and operation of the interferometer units of the optical tomographic imaging apparatus 500 will be described taking the interferometer unit 25a as an example. The interferometer unit 25a includes: a beam splitting means 3a that splits the light beam La outputted from the light source 10a into a measuring beam L1a and a reference beam L2a; a beam combining means 4a that combines a reflected beam L3a from a measuring object S when the measuring beam L1a is irradiated on the measuring object S with the reference beam L2a; and an interference beam detection means 40a that detects an interference beam L4a produced when the beams are combined as an interference signal ISa. It is noted that the light beams are omitted in FIG. 13.

The light beam La outputted from the light source 10a is guided through the optical fiber FB1a, and split into the measuring beam L1a and reference beam L2a in the beam splitting means 3a. The measuring beam L1a is outputted to an optical fiber FB2a and the reference beam L2a is outputted to an optical fiber FB3a. The measuring beam L1a is guided through the optical fiber FB2a, passed through a circulator 5a, guided by the optical fiber FB4a and outputted from the interferometer 25a, and inputted to the beam combining means 15a.

The reflected beam L3a from the measuring object S when the measuring beam L1a is irradiated on the measuring object S is guided through the optical fiber FB4a in the reverse direction of the measuring beam L1a and inputted to the interferometer unit 25a, passed through the circulator 5a, guided through the optical fiber FB5a, and inputted to the beam combining means 4a.

In the mean time, the reference beam L2a split by the beam splitting means 3a is inputted to the beam combining means 4a after the optical path length thereof is controlled by an optical path length control means 20a provided in the middle of the optical fiber FB3a.

In the beam combining means 4a, the reflected beam L3a and reference beam L2a are combined together, and the interference beam L4a produced when the beams are combined is divided into halves and outputted to the interference beam detection means 40a. The interference signal ISa obtained in the interference beam detection means 40a is outputted to the tomographic image processing means 50. The structures and operations of the interference beam detection means 40a and tomographic image processing means 50 are identical to those of the first embodiment.

In the optical tomographic imaging apparatus 500, the spectrum of each of the light beams La, Lb, Lc, and Ld outputted from the light sources 10a, 10b, 10c, and 10d respectively, method of wavelength sweep of each light source, and synchronization method performed by the control means 16 are identical to those of the first embodiment.

In the fifth embodiment, the beam combining means 15a combines the measuring beam split by the interferometer unit 25a with the measuring beam split by the interferometer unit 25c, and the beam combining means 15b combines the measuring beam split by the interferometer unit 25b with the measuring beam split by the interferometer unit 25d. Further, in the fifth embodiment, the control means 16 controls each measuring beam in the downstream of the beam combining means 15a, 15b such that at least one of the measuring beams is irradiated on the measuring object at a time period which is different from a time period in which another one or more of the measuring beams are irradiated on the measuring object, and two or more of the measuring beams having different wavelengths from each other are combined and irradiated on the measuring object at the same time. Here, the control means 16 causes measuring beams having separate wavelength ranges from each other are irradiated on the measuring object S at the same time, and measuring beams having partially overlapping wavelength ranges with each other are irradiated on the measuring object S during different time periods.

In the present embodiment, it is noted that the control means 16, and beam combining means 15a, 15b function also as reflected beam separation means. That is, the respective reflected beams when the respective measuring beams are irradiated on the measuring object S are separated from each other by the control means 16 according to the time, and further separated from each other by the beam combining means 15a, 15b according to the wavelength, and inputted to the respective interferometer units.

In each interferometer unit, each reflected beam is combined with each reference beam by the beam combining means, and the interference beam produced when the beams are combined is detected by the interference beam detection means as the interference signal. Each interference signal is outputted to the tomographic image processing means 50, which generates a tomographic image of the measuring object S using the interference signals.

Consequently, the optical tomographic imaging apparatus 500 may provide advantageous effects identical to those of the optical tomographic imaging apparatus 1. Further, the optical tomographic imaging apparatus 500 includes an interferometer unit for each light beam, so that each interferometer unit may be structured optimally according to the wavelength range of each light beam, thereby resolution of a tomographic image to be obtained may be improved. Still further, in the optical tomographic imaging apparatus 500, the control means 16 and beam combining means 15a, 15b may act also as the reflected beam separation means.

It is noted that the structure in which the order of the beam combining means and control means having wavelength selectivity shown in FIG. 11 is changed or a control means that individually controls the emission/extinction of the light sources of the light emission section like that shown in FIG. 12 may be applied to the structure in which an interferometer is provided for each light beam outputted from each light source as in the optical tomographic imaging apparatus 500.

In the first to fifth embodiment, the description has been made of a case in which Mach-Zehnder interferometers are used, but Fizeau interferometers or Michelson interferometers may also be used.

When the first to fifth embodiments of the present invention are compared with a conventional method in which light beams having different wavelengths are sequentially outputted one at a time using only a switching element, the method of the present invention may perform measurement faster than the conventional method. Further, when the first to fifth embodiments of the present invention are compared with a method in which separation of the reference beams and reflected beams using only branching means such as WDM couplers, the present invention, which separates the beams according to the time using the control means for the region where wavelength ranges are overlapping with each other, may reduce light loss to substantially zero.

Further, when the embodiments of the present invention are compared with the conventional technology, the conventional apparatus is structured such that the entire wavelength range of the light outputted from the light source unit needs to be covered by a single detector, and where broadband light is outputted from the light source unit, it has been difficult to find a photodiode which is usable for a detector meeting the broadband, and sometimes there has been a case in which an apparatus capable of performing broadband measurement is not constructed. In contrast, according to the configurations of the apparatuses according to the embodiments of the present invention, each detector does not need to meet the entire wavelength range of the light outputted from the light source unit, so that an apparatus capable of performing broadband measurement may be constructed, and at the same time required specifications of the optical component arts used may be relaxed, thereby the component cost may be reduced.

Where an optical tomographic imaging apparatus of the present invention is applied to an endoscope, if a light beam with a wavelength within a wavelength range which may be sensed by the CCD mounted in the endoscope, for example, a light beam with a center wavelength of 800 nm, is used as the light beam of a wavelength combined light source, the light beam may be used also as the aiming light, so that a separate aiming light source will not be required.

In the optical tomographic imaging apparatus, if light beams having the spectra shown in FIG. 6 are used, the spectrum formed by the light beams outputted from the light source unit is discontinuous. In the past, it has been thought to be ideal that the light source used for the OCT system have a Gaussian shape spectrum. In the TD-OCT system, the use of a light source having a spectrum shape departing from the Gaussian shape poses a problem that the resolution of the image is degraded due to the development of sidelobes. In the FD-OCT measurement that measures spectrum signals, the spectrum of the light source is measured in advance, and interference signals are multiplied by a filter function obtained by the measurement, thereby the interference signals are approximated to those obtainable if the spectrum had a Gaussian shape. But, the spectrum of the light source corresponding to the depth range for obtaining a tomographic image is required to be continuous. For example, a discrete spectrum shape in which the light intensity becomes zero in the middle of the emission band has been thought to be inappropriate for proper processing.

That is, Fourier transform method in OCT measurement requires that the spectrum of the light source is continuous and broadband. Therefore, the light source unit 10 that outputs discrete light beams La and Lb has been though not to be suitable as the conventional OCT light source for obtaining a tomographic image.

As clear from the description of the tomographic image processing means 50, it has been found that a high resolution tomographic image without sidelobes may be obtained even when a light source unit that forms a discontinuous spectrum, instead of a continuous spectrum, is used. This may eliminate the necessity to use a specific light source unit having particular characteristics described above.

The optical tomographic imaging apparatus according to each of the first to eight embodiments is a SS-OCT system. As described in the section under "Description of the Related Art", the SS-OCT system is superior to the SD-OCT system in measuring rate. More specifically, assuming, for example, an OCT system with a wavelength range of 200 nm and a wavelength resolution of 0.1 nm, more than 2000 data points are required in order to obtain a high resolution optical tomographic image, and more than 4000 data points are desirable in order to know the spectral shape more accurately. Further, it is desirable that the OCT system may display a two dimensional tomographic image as a motion image. For example, when an image with 2000 data points within the measuring wavelength range and 1000 lines in the direction orthogonal to the optical axis is displayed at an iteration rate of 10 Hz, a data readout rate of 20 MHz is required.

As described above, in the SD-OCT system, in order to increase the number of data points, it is necessary to increase the number of elements of the detector. One of the currently available detector arrays of InGaAs elements having light receiving sensitivity at near infrared region is a detector array with 1024 elements (for example, Model Number: SU-LDV-1024LE, manufactured by Sensors Unlimited Inc.), but such detector array is expensive. In order to obtain more than 2000 data points, or more than 4000 data points, at least two, and preferably four expensive 1024-element detector arrays are required. Further, highly accurate positional alignment is required when a plurality of detector arrays is connected. Still further, the comparison result of the specifications between the 1024-element detector array described above and a 512-element detector array (Model Number: SU-LDV-512LD, manufactured by Sensors Unlimited Inc.) shows that the maximum line rate is 12820 frames/second for the 512-element detector array, while that of the 1024-element detector array is 4266 frames/second, which shows that the readout rate for a single line decreases as the number of elements is increased. The decrease in the readout rate for a single line poses a problem that the frame rate of an image is decreased.

In contrast, in the SS-OCT system, the increase in the data points may be realized inexpensively by increasing the sampling interval of the detector. In the example described above, when an image with 1000 lines in the direction orthogonal to the optical axis is displayed at an iteration rate of 10 Hz, if data points are 4000, then data need to be obtained with a sampling rate of 40 MHz, which may be readily realized with a single photodiode element and an inexpensive electrical circuit.

When broadening the bandwidth of the measuring beam, the SD-OCT system requires an optical design change, such as a wavelength dispersion element, such as grating, of the interference beam detection means, and light focusing element, such as a lens, whereas in the SS-OCT system, the broadening of the bandwidth may be realized easily, since it only requires the addition of a WDM coupler and a detector.

It will be appreciated that the present invention is not limited to the embodiments described above, and various changes and modifications may be made in the invention without departing from the scope and spirit thereof. For example, in each of the embodiments, the description has been made of a case in which a single light beam is outputted from a single light source. But a multi-color light source that outputs a plurality of light beams having different wavelengths may be used.

In the aforementioned examples, the description has been made of a case in which four light beams are combined by the light control unit, but the number of light beams to be combined may be three, or not less than five. Where may light beams are combined, the light control unit may be constructed using, for example, an n×1 WDM coupler or a plurality of WDM couplers.

Figure 14:
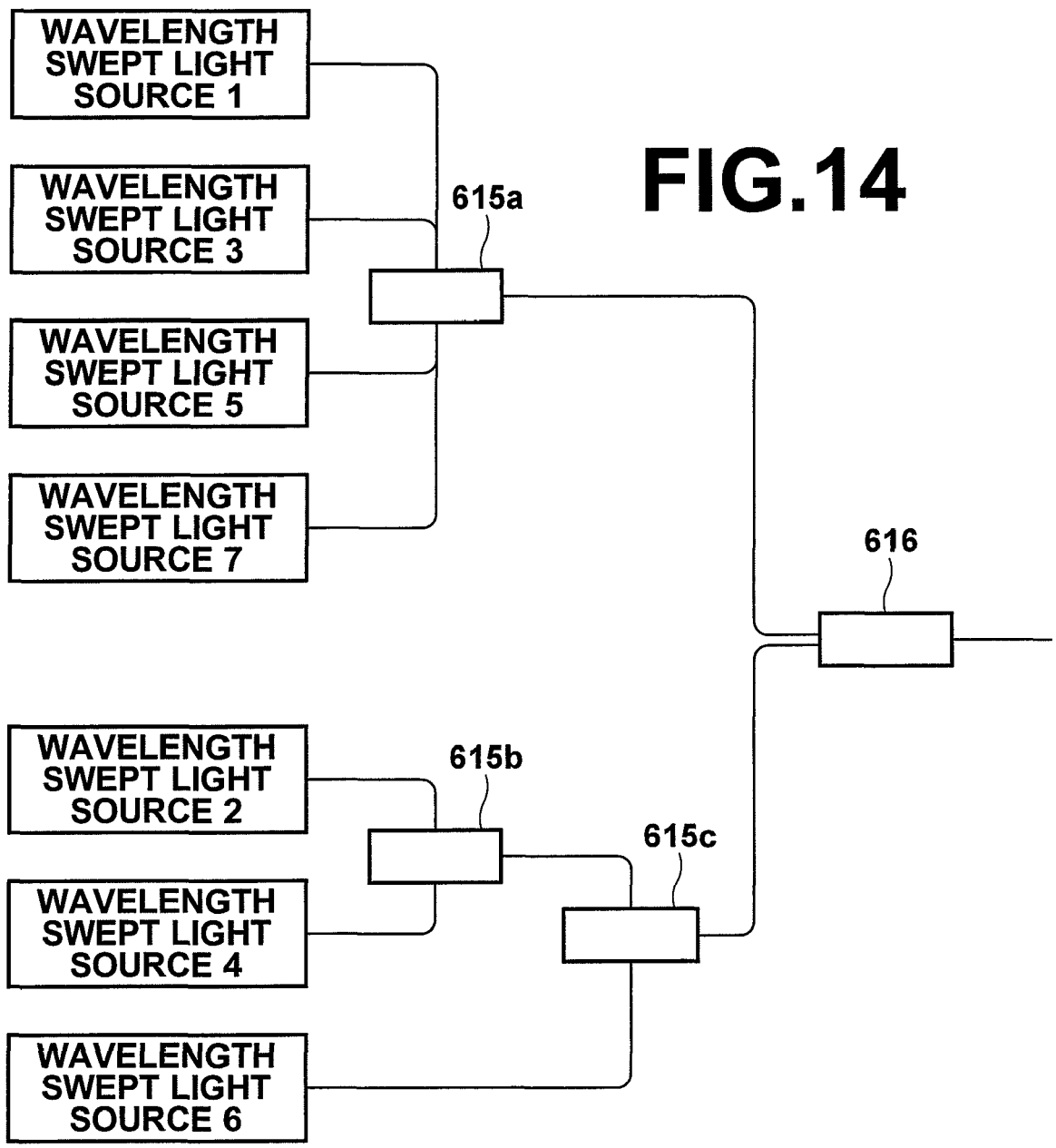
FIG. 14 illustrates an example method for combining light beams from seven light sources.

FIG. 14 conceptually illustrates an example structure of the light control unit that combines and outputs light beams outputted from seven wavelength swept light sources 1 to 7. Here, the wavelength swept light sources 1 to 7 have different wavelength ranges from each other, and the center wavelengths of the wavelength ranges become longer in this order. The light beams adjacent to each other in the order of the center wavelength have partially overlapping wavelength ranges, and the light beams not adjacent to each other in the order of the center wavelength have separated wavelength ranges. In this case, for example, a configuration may be adopted in which the light beams from the wavelength swept light sources 1, 3, 5, and 7 are combined by a 4×1 WDM coupler 615a, the light beams from the wavelength swept light sources 2 and 4 are combined by a 2×1 WDM coupler 615b, and the light beam from the wavelength swept light source 6 and the light beams combined by the WDM coupler 615b are combined by a WDM coupler 615c. Then, the light beams combined by the WDM coupler 615a and WDM coupler 615c are inputted to the control means 616. Thereafter, from the control means 616, light beams having separate wavelength ranges are outputted during the same time period and light beams having partially overlapping wavelength ranges are outputted during different time periods.

In the embodiments, the description has been made of a case in which fiber ring type wavelength swept light sources are used in the light source unit. But other types of wavelength swept light sources may also be used. For example, a wavelength swept light source that uses a diffraction grating, polygon, bandpass filter, or the like as the wavelength selection means, and a rare-earth doped optical fiber, or the like as the gain medium may also be used. The wavelength sweep is desirable to be continuous, but it may be such sweep as to cause discontinuous wavelength changes. The wavelength sweep periods are desirable to be the same for the light beams outputted during the same time period, but they may be different from each other for the light beams outputted during different time periods.

The spectrum of each light beam is not limited to that described above. If wavelengths of at least two of all of the light beams are partially overlapping with each other, and wavelengths of at least two of all of the light beams are separated from each other, the advantageous effects of the beam combining means and control means having wavelength selectivity described above may be obtained.

Further, in the embodiments, the description has been made of a case in which the spectrum of each of the light beams outputted from the light source unit has substantially a Gaussian shape, but the shape is not limited to this. For example, the light beam may have a spectrum having a constant light intensity with respect to each wavelength.

Further, in the embodiments, the description has been made of a case in which the light beams are guided by the optical fiber, and combined or split by the optical coupler or WDM coupler. Alternatively, a bulk optical system may be employed in which beam combining and splitting is performed spatially using a mirror, prism, dichroic mirror, dichroic prism, or the like.

Still further, in the embodiments, the description has been made of a case in which the reflected beams from the measuring object or back scattered light beams are measured. Where the measuring object is a transparent medium, such as a glass block, transparent film, or the like, and the in-plane refractive index distribution, thickness distribution, birefringence, or the like is obtained, transmitted beams are measured instead of reflected beams. In such a case, the transmitted beams may be guided to the beam combining means, instead of reflected beams, and combined with the reference beams. Here, the other structures and methods described in the embodiments may be applied as they are.

What is claimed is:

1. An optical tomographic imaging apparatus, comprising:
   a light control unit that combines and outputs a plurality of light beams, which includes: a light emission section capable of outputting three or more light beams swept in wavelength within different wavelength ranges from each other; a wavelength combining means having wavelength selectivity, that combines and outputs at least two of the three or more light beams; and a control means that performs control in the light emission section, or upstream or downstream of the wavelength combining means in the optical path of the light beams to cause at least one light beam is outputted during a time period which is different from a time period in which another one or more light beams are outputted, thereby causing two or more light beams having different wavelengths from each other to be combined and outputted at the same time;
   a beam splitting means that splits each of the light beams outputted from the light control unit into a measuring beam and a reference beam;
   a beam combining means that combines the reference beams with reflected beams from a measuring object when the measuring beams are irradiated on the measuring object with respect to each of the light beams;
   an interference beam detection means that detects interference beams produced when the reflected beams are combined with the reference beams by the beam combining means as interference signals with respect to each of the light beams; and
   a tomographic image processing means that generates a tomographic image of the measuring object using the interference signals.

2. The optical tomographic imaging apparatus of claim 1, wherein:
   the wavelength ranges of at least two of the three or more light beams are separated from each other;
   the wavelength ranges of at least two of the three or more light beams are partially overlapping with each other; and
   the control means is a means that causes the light beams having separate wavelength ranges to be outputted during the same time period, and the light beams having partially overlapping wavelength ranges to be outputted during different time periods.

3. An optical tomographic imaging apparatus, comprising:
   a light emission section capable of outputting three or more light beams swept in wavelength within different wavelength ranges from each other, and outputs at least two or more of the three or more light beams;
   a beam splitting means that splits each of the light beams outputted from the light emission section into a measuring beam and a reference beam;
   a wavelength combining means having wavelength selectivity, that combines and outputs at least two of a plurality of split measuring beams;
   a control means that performs control in the light emission section, or upstream or downstream of the wavelength combining means in the optical path of the measuring beams to cause at least one measuring beam is irradiated on a measuring object during a time period which is different from a time period in which another one or more measuring beams are irradiated, and two or more measuring beams having different wavelengths from each other to be combined and irradiated on the measuring object at the same time;
   a beam combining means that combines the reference beams with reflected beams from the measuring object when the combined measuring beams are irradiated on the measuring object with respect to each of the light beams;
   an interference beam detection means that detects interference beams produced when the reflected beams are combined with the reference beams by the beam combining means as interference signals with respect to each of the light beams; and
   a tomographic image processing means that generates a tomographic image of the measuring object using the interference signals.

4. The optical tomographic imaging apparatus of claim 3, wherein:
   the wavelength ranges of at least two of the three or more light beams are separated from each other;
   the wavelength ranges of at least two of the three or more light beams are partially overlapping with each other; and
   the control means is a means that causes the light beams having separate wavelength ranges to be irradiated on the measuring object during the same time period, and the light beams having partially overlapping wavelength ranges to be irradiated on the measuring object during different time periods.

5. An optical tomographic imaging method, comprising the steps of:

provide a light emission section capable of outputting three or more light beams swept in wavelength within different wavelength ranges from each other, and outputs at least two or more of the three or more light beams;

splitting each of the light beams outputted from the light emission section into a measuring beam and a reference beam;

combining and outputting at least two of a plurality of split measuring beams using a wavelength combining means having wavelength selectivity;

causing, in the light emission section, or upstream or downstream of the wavelength combining means in the optical path of the measuring beams, at least one measuring beam to be irradiated on a measuring object during a time period which is different from a time period in which another one or more measuring beams are irradiated, and two or more measuring beams having different wavelengths from each other to be combined and irradiated on the measuring object at the same time;

combining the reference beams with reflected beams from the measuring object when the combined measuring beams are irradiated on the measuring object with respect to each of the light beams;

detecting interference beams produced when the reflected beams are combined with the reference beams as interference signals with respect to each of the light beams; and generating a tomographic image of the measuring object using the interference signals.

6. The optical tomographic imaging method of claim 5, wherein:

at least two of the three or more light beams have separate wavelength ranges from each other;

at least two of the three or more light beams have partially overlapping wavelength ranges; and the light beams having separate wavelength ranges are irradiated on the measuring object during the same time period, and the light beams having partially overlapping wavelength ranges are irradiated on the measuring object during different time periods.

* * * * *